United States Patent
Yasugi et al.

(10) Patent No.: US 9,181,328 B2
(45) Date of Patent: Nov. 10, 2015

(54) HUMAN MONOCLONAL ANTIBODIES BROADLY PROTECTIVE AGAINST INFLUENZA B VIRUS AND METHODS OF USING THE SAME

(71) Applicants: **OSAKA

Fig. 1

```
B_Florida_HA.gpt     1:DRICTGITSSNSPHVVKTATQGEVNVTGVIPLTTTPTKSYFANLKGTRTRGKLCPDCLNC 60
3A2_Esc.gpt           :-RICTGITSSNSPHVVKTATQGEVNVTGVIPLTTTPTKSYFANLKGTRTRGKLCPDCLNC
10C4_Esc.gpt          :DRICTGITSSNSPHVVKTATQGEVNVTGVIPLTTTPTKSYFANLKGTRTRGKLCPDCLNC 61:TDLDVALGRPMCVGTTPSAKASILHEVKPVTSGCFPIMHDRTKIRQLPNLLRGYENIRLS 120
                      :TDLDVALGRPMCVGTTPSAKASILHEVKPVTSGCFPIMHDRTKIRQLPNLLRGYENIRLS
                      :TDLDVALGRPMCVGTTPSAKASILHEVKPVTSGCFPIMHDRTKIRQLPNLLRGYENIRLS 121:TQNVIDAEKAPGGPYRLGTSGSCPNATSKSGFFATMAWAVPKDNNKNATNPLTVEVPYIC 178
                      :TQNVIDAEKAPGGPYRLGTSGSCPNATSKSGFFATMAWAVPKDNNKNATNPLTVEVPYIC
                      :TQNVIDAEKAPGGPYRLGTSGSCPNATSKSGFFATMAWAVPKDNNKNATNPLTVEVPYIC 179:TEGEDQITVWGFHSDDKTQMKNLYGDSNPQKFTSSANGVTTHYVSQIGSFPDQTEDGGLP 238
                      :TEGEDQITVWGFHSDNKIQMKNLYGDSNPQKFTSSANGVTTHYVSQIGSFPDQTEDGGLP
                      :TEGEDQITVWGFHSDNKNQMKNLYGDSNPQKFTSSANGVTTHYVSQIGSFPDQTEDGGLP
                                      * *
                   239:QSGRIVVDYMMQKPGKTGTIVYQRGVLLPQKVWCASGRSKVIKGSLPLIGEADCLHEKYG 298
                      :QSGRIVVDYMMQKPGKTGTIVYQRGVLLPQKVWCASGRSKVIKGSLPLIGEADCLHEKYG
                      :QSGRIVVDYMMQKPGKTGTIVYQRGVLLPQKVWCASGRSKVIKGSLPLIGEADCLHEKYG 299:GLNKSKPYYTGEHAKAIGNCPIWVKTPLKLANGTKYRPPAKLLKERGFFGAIAGFLEGGW 358
                      :GLNKSKPYYTGEHAKAIGNCPIWVKTPLKLANGTKYRPPAKLLKERGFFGAIAGFLEGGW
                      :GLNKSKPYYTGEHAKAIGNCPIWVKTPLKLANGTKYRPPAKLLKERGFFGAIAGFLEGGW 359:EGMIAGWHGYTSHGAHGVAVAADLKSTQEAINKITKNLNSLSELEVKNLQRLSGAMDELH 418
                      :EGMIAGWHGYTSHGAHGVAVAADLKSTQEAINKITKNLNSLSELEVKNLQRLSGAMDELH
                      :EGMIAGWHGYTSHGAHGVAVAADLKSTQEAINKITKNLNSLSELEVKNLQRLSGAMDELH 419:NEILELDEKVDDLRADTISSQIELAVLLSNEGIINSEDEHLLALERKLKKMLGPSAVEIG 478
                      :NEILELDEKVDDLRADTISSQIELAVLLSNEGIINSEDEHLLALERKLKKMLGPSAVEIG
                      :NEILELDEKVDDLRADTISSQIELAVLLSNEGIINSEDEHLLALERKLKKMLGPSAVEIG 479:NGCFETKHKCNQTCLDRIAAGTFNAGEFSLPTFDSLNITAASLNDDGLDNHTILLYYSTA 538
                      :NGCFETKHKCNQTCLDRIAAGTFNAGEFSLPTFDSLNITAASLNDDGLDNHTILLYYSTA
                      :NGCFETKHKCNQTCLDRIAAGTFNAGEFSLPTFDSLNITAASLNDDGLDNHTILLYYSTA 539:ASSLAVTLMLAIFIVYMVSRDNVSCSICL    (SEQ ID No: 29)             567
                      :ASSLAVTLMLAIF----------------    (SEQ ID No: 30)
                      :ASSLAVTLMLAIF----------------    (SEQ ID No: 31)
```

| I | H | R | L | G | V | D |

| T | Y | K | P | S | M | E |

Flo/06

Fig. 11

```
  1  ATGGAGTTTGGGCTGAGCTGGGTTCTCCTCGTTGCTCTTTTAAGAGGTGTCCAGTGTCAG  60
     M  E  F  G  L  S  W  V  L  L  V  A  L  L  R  G  V  Q  C  Q

61  GTGCAGCTGGTGGAGTCTGGGGGAGACGTGGTCCAACCTGGGAGGTCCCTGAGACTCTCC  120
     V  Q  L  V  E  S  G  G  D  V  V  Q  P  G  R  S  L  R  L  S

121  TGCGCAGCGTCTGGATTCACCTTCAATAACTATGGCATGCACTGGGTCCGCCAGGCTCCA  180
     C  A  A  S  G  F  T  F  N  N  Y  G  M  H  W  V  R  Q  A  P

181  GGCAAGGGGCTGGAGTGGGTGGCAGTTGTCTGGTATGATGGACTTATTAAATACTATGCG  240
     G  K  G  L  E  W  V  A  V  V  W  Y  D  G  L  I  K  Y  Y  A

241  GACTCCGTGAAGGGCCGATTCACCATCTCCAGAGACAATTCgAAAAACACCCTGTATCTG  300
     D  S  V  K  G  R  F  T  I  S  R  D  N  S  K  N  T  L  Y  L

301  CAAATGAACACCCTGAGAGCCGAGGACATGGGTGTCTATTACTGTGCGAGAGATCTACAG  360
     Q  M  N  T  L  R  A  E  D  M  G  V  Y  Y  C  A  R  D  L  Q

361  CCTCCCCATTCACCCTACGGTATGGACGTCTGGGGCCAAGGGACCACGGTCACCGTCTCC  420
     P  P  H  S  P  Y  G  M  D  V  W  G  Q  G  T  T  V  T  V  S

421  TCA  (SEQ ID No. 32)
     S    (SEQ ID No. 33)
```

The variable region of the heavy chain (5A7)

```
  1  ATGGCCTGGGTCTCATTCTACCTCACCCTCCTCACTCACTGTGCAGGGTCCTGGGCCCAG  60
     M  A  W  V  S  F  Y  L  T  L  L  T  H  C  A  G  S  W  A  Q

61  TCTGTGCTGACTCAGCCACCCTCAGCGTCTGGGACCCCCGGGCAGAGGGTCACCATCTCT  120
     S  V  L  T  Q  P  P  S  A  S  G  T  P  G  Q  R  V  T  I  S

121  TGTTCTGGAAGCAGCTCCAACATCGGAAGTAATGATGTCTATTGGTACCAGAACCTCCCA  180
     C  S  G  S  S  S  N  I  G  S  N  D  V  Y  W  Y  Q  N  L  P

181  GGAACGGCCCCCAAACTCCTCATCTATAATAATAATCAACGGCCCTCAGGGGTCCCTGAC  240
     G  T  A  P  K  L  L  I  Y  N  N  N  Q  R  P  S  G  V  P  D

241  CGATTCTCTGGCTCCAAGTCTGGCACCTCAGCCTCCCTGGCCATCAGTGGGCTCCGGTCC  300
     R  F  S  G  S  K  S  G  T  S  A  S  L  A  I  S  G  L  R  S

301  GAGGATGAGGCTGATTATTATTGTGCAGCATGGGATGACAGCCTGACTGTCTCCTTCGGA  360
     E  D  E  A  D  Y  Y  C  A  A  W  D  D  S  L  T  V  S  F  G

361  ACTGGGACCAAGGTCACCGTCCTAGGT  (SEQ ID No. 34)
     T  G  T  K  V  T  V  L  G   (SEQ ID No. 35)
```

The variable region of the lamda chain (5A7)

Fig. 12

```
  1 ATGAAACACcTGTGGTTCTTCCTCcTCCTGGTGGCAGCTCCCAGATGGGTCCTGTCCCAG  60
    M  K  H  L  W  F  F  L  L  L  V  A  A  P  R  W  V  L  S  Q

61 GTGCAGCTGGTGGAGTCGGGCCCAGGACTGGTGAAGCCTTCTGAGACCCTGTCCCTCACC 120
    V  Q  L  V  E  S  G  P  G  L  V  K  P  S  E  T  L  S  L  T

121 TGCACTGTCTCTAGTGGCTCCATCAGTAGTTACTACTGGAGCTGGATCCGGCAGCCCCCC 180
    C  T  V  S  S  G  S  I  S  S  Y  Y  W  S  W  I  R  Q  P  P

181 GGGAAGGGACTGGAGTGGATTGGGTATGTCTATAACAGTGGGAGTACCAGGTACAACCCC 240
    G  K  G  L  E  W  I  G  Y  V  Y  N  S  G  S  T  R  Y  N  P

241 TCCCTCAAGAGTCGCCTCACCATGTCAGTGGACGCGTCCAGGAAGCAGGTCTCCCTGAAG 300
    S  L  K  S  R  L  T  M  S  V  D  A  S  R  K  Q  V  S  L  K

301 TTGAGCTCTGTGAGTGCTGCGGACACGGCCGTGTATTACTGTGCGAGAGCCCCGGACGAT 360
    L  S  S  V  S  A  A  D  T  A  V  Y  Y  C  A  R  A  P  D  D

361 TACTATGATAGTGTTGGTTATTACTACGGATGTCCGTACTTCGACTCCTGGGGCCAGGGA 420
    Y  Y  D  S  V  G  Y  Y  Y  G  C  P  Y  F  D  S  W  G  Q  G

421 ACCCTGGTCACCGTCTCCTCA    (SEQ ID No. 36)
    T  L  V  T  V  S  S    (SEQ ID No. 37)
```

The variable region of the heavy chain (3A2)

```
  1 ATGGAAGCCCCAGCGCAGCTTCTCTTCCTCCTGCTACTCTGGCTCCCAGATACCAGTGGA  60
    M  E  A  P  A  Q  L  L  F  L  L  L  L  W  L  P  D  T  S  G

61 GAAATAGGGATGACGCAGTCTCCAGCCACCCTGTCTGTGTCTCCAGGGGAAAGAGCCACC 120
    E  I  G  M  T  Q  S  P  A  T  L  S  V  S  P  G  E  R  A  T

121 CTCTTTTGCAGGGCCAGTCCGAGTATTAGCGACAACTTAGCCTGGTACCAGCAGAAACCT 180
    L  F  C  R  A  S  P  S  I  S  D  N  L  A  W  Y  Q  Q  K  P

181 GGCCAGGCTCCCAGGCTCCTCTTCTATGGTGCATCCACCAGGGCCACTGGTATCCCAGCC 240
    G  Q  A  P  R  L  L  F  Y  G  A  S  T  R  A  T  G  I  P  A

241 AGGTTCAGCGGCAGTGGGTCTGGGACAGAGTTCACTCTCACCATCAGCAGTGTGCAGTCT 300
    R  F  S  G  S  G  S  G  T  E  F  T  L  T  I  S  S  V  Q  S

301 GAAGATATTGGAGTTTATTATTGTCAGCAGTATAGTAACTGGCCTCGTACTTTTGGCCAG 360
    E  D  I  G  V  Y  Y  C  Q  Q  Y  S  N  W  P  R  T  F  G  Q

361 GGGACCAAGCTGCAGATCAAA    (SEQ ID No. 38)
    G  T  K  L  Q  I  K    (SEQ ID No. 39)
```

The variable region of the kappa chain (3A2)

Fig. 13

```
  1 ATGGAGTTTGGGCTGAGCTGGCTTTTTCTTGTGGCTATTTTAAAAGGTGTCCAGTGTGAG  60
    M  E  F  G  L  S  W  L  F  L  V  A  I  L  K  G  V  Q  C  E

61 GTGCAGCTGTTGGAGTCTGGGGGAGGCTTGGTCCAGCCGGGGGGGTCCCTGAGACTCTCC 120
    V  Q  L  L  E  S  G  G  G  L  V  Q  P  G  G  S  L  R  L  S

121 TGTGCAGCCTCTGGATTCACCTTTAGCAACTATGCCATGAGCTGGGTCCGCCAGGCTCCA 180
    C  A  A  S  G  F  T  F  S  N  Y  A  M  S  W  V  R  Q  A  P

181 GGGAAGGGGCTGGAGTGGGTCTCAGCTATTAGTGGTGGTGGTGATTGGACATACTACGCA 240
    G  K  G  L  E  W  V  S  A  I  S  G  G  G  D  W  T  Y  Y  A

241 GACTCCGTGAAGGGCCGATTCTCCATCTCCAGCGACAATTCCAAGAACACGCTGTATCTG 300
    D  S  V  K  G  R  F  S  I  S  S  D  N  S  K  N  T  L  Y  L

301 CAAATGAACAGCCTGAGAGCCGAGGACACGGCCGTATATTACTGTGCGAAAGATGTCACG 360
    Q  M  N  S  L  R  A  E  D  T  A  V  Y  Y  C  A  K  D  V  T

361 TATTTGTATGACAGTAGTGGTTATTACTACGGGGGAGCCGACCGCGATTATTACTTTGAC 420
    Y  L  Y  D  S  S  G  Y  Y  Y  G  G  A  D  R  D  Y  Y  F  D

421 TACTGGGGCCAGGGAACCCTGGTCACCGTCTCCTCA          (SEQ ID No. 40)
    Y  W  G  Q  G  T  L  V  T  V  S  S              (SEQ ID No. 41)
```

The variable region of the heavy chain (10C4)

```
  1 ATGCCCTGGGCTCTTCTCCTCCTCACCCTCCTCACTCACTGTGCAGGGTCCTGGGCCCAG  60
    M  P  W  A  L  L  L  L  T  L  L  T  H  C  A  G  S  W  A  Q

61 TCTGTGCTGACTCAGCCACCCTCAGCGTCTGGGACCCCCGGGCAGAGGGTCTCCATCTCT 120
    S  V  L  T  Q  P  P  S  A  S  G  T  P  G  Q  R  V  S  I  S

121 TGTTCTGGAGGCAGCTCCAACATCGGAAGTAATACTGTAAACTGGTACCAGCAGCTCCCA 180
    C  S  G  G  S  S  N  I  G  S  N  T  V  N  W  Y  Q  Q  L  P

181 GGAACGGCCCCCAGACTCCTCATCTATAGCAATAATCAGCGGCCCTTAGGGGTCCCTGAC 240
    G  T  A  P  R  L  L  I  Y  S  N  N  Q  R  P  L  G  V  P  D

241 CGATTCTCTGAGTCCAAGTCTGGCACCTCAGCCTCCCTGGCCATCAGTGGGCTCCGGTCT 300
    R  F  S  E  S  K  S  G  T  S  A  S  L  A  I  S  G  L  R  S

301 GAGGATGAGGCTGATTATTACTGTGCTGCATGGGATGACAGCCTGAATGGTTGGGTGTTC 360
    E  D  E  A  D  Y  Y  C  A  A  W  D  D  S  L  N  G  W  V  F

361 GGCGGAGGGACCAGGCTGACCGTCCTAGGT   (SEQ ID No. 42)
    G  G  G  T  R  L  T  V  L  G      (SEQ ID No. 43)
```

The variable region of the lamda chain (10C4)

HUMAN MONOCLONAL ANTIBODIES BROADLY PROTECTIVE AGAINST INFLUENZA B VIRUS AND METHODS OF USING THE SAME

GOVERNMENT FUNDING

The subject matter described herein was supported, at least in part, by the Japan Science and Technology Agency/Japan International Cooperation Agency, Science and Technology Research Partnership for Sustainable Development (JST/JICA, SATREPS); and a Grant-in-Aid for Young Scientists (B) from the Japan Society for the Promotion of Science to Mayo Yasugi.

CROSS REFERENCE TO RELATED APPLICATIONS

This is a National Stage of International Application No. PCT/JP2013/000538 filed Jan. 31, 2013, claiming priority based on U.S. Provisional Application No. 61/592,657 filed Jan. 31, 2012, the contents of all of which are incorporated herein by reference in their entirety.

TECHNICAL FIELD

The present invention relates to materials and methods for the treatment of influenza B viral infections in humans.

BACKGROUND ART

The ability of influenza virus to evade immune surveillance through rapid genetic drift and reassortment means that it remains a continuous public health threat. During annual epidemics five to fifteen percent of the worldwide population are typically infected, resulting in three million to five million cases of severe illness and between 250,000 to 500,000 deaths per year (Lambert et al., The New England Journal of Medicine 363:2036-2044; WHO, Influenza (Seasonal) Fact Sheet No. 211). Influenza B virus, like H1 and H3 subtypes of influenza A virus, has caused epidemics in humans (WHO, Influence (Seasonal) Fact Sheet No. 211). In contrast to influenza A, influenza B virus is found almost exclusively in humans and has a much slower mutational rate than that observed for influenza A virus (Carrat et al., Vaccine 25:6852-6862; Nobusawa et al., Journal of Virology 80:3675-3678; Webster et al, The Journal of General Virology 54:243-251). However, co-circulation of two phylogenetically and antigenically distinct lineages, represented by the B/Yamagata/16/88 and B/Victoria/2/87, has caused antigenic variation through genetic reassortment and antigenic drift from cumulative mutations, leading to annual endemics (Hay et al., Philosophical Transactions of the Royal Society of London 356:1861-1870; Lin et al., Virus Research 103:47-52).

The development of vaccines producing broadly reactive antibodies and therapeutic strategies using human monoclonal antibodies (HuMAbs) with global reactivity has recently been gathering great interest. Neuraminidase inhibitors oseltamivir (Tamiflu) and zanamivir (Relenza) have been widely used for the treatment of influenza viral infection. However, they have limited efficacy when administered more than 48 hours after the onset of illness (Aoki et al., The Journal of Antimicrobial Chemotherapy 51: 123-129), and widespread use has resulted in the emergence of resistant viral strains (Kiso et al, Lancet 364:759-765; Lowen et al., Infectious Disorders Drug Targets 7:318-328; Reece, Journal of Medical Virology 79:1577-1586). Therefore, new therapeutic strategies that provide potent and broadly cross-protective host immunity are a global public health priority. Thus, the development of novel antibody-based therapies is of great interest (Marasco et al., Nature Biotechnology 25:1421-1434).

Several human monoclonal antibodies (HuMAbs) with broad neutralizing activities were identified against the hemagglutinin (HA) protein in influenza A viruses, including C6261 and F10, which react with group 1 viruses (Ekiert et al., Science 324:246-251; Sui et al., Nature Structural & Molecular Biology 16:265-273), and CR8020, which neutralizes group 2 viruses (Ekiert et al., Science 333:843-850). Another HuMAb, FI6v3, which neutralized both group 1 and group 2 influenza A viruses, was isolated in 2011 (Corti et al., Science 333: 850-856). Although influenza B virus has a much slower mutational rate than that observed for influenza A virus like H1 and H3 subtypes, it has annually caused epidemics in humans (NPL1: Hay et al., Philosophical Transactions of the Royal Society of London 256:1861-1870; NPL2: Lin et al., Virus Research 103:47-52). For influenza B virus, however, broadly neutralizing HuMAbs, CR8033, CR8071 and CR9114, have firstly reported on September 2012 (NPL3: Dreyfus et al., Science 337: 1343-1348). Accordingly, a need exists for broadly neutralizing HuMAb against the influenza B virus.

CITATION LIST

Non Patent Literature

[NPL 1] Hay et al., Philos Trans R Soc Lond B Biol Sci. 2001 Dec. 29; 356(1416): 1861-1870.
[NPL 2] Lin et al., Virus Res. 2004 July; 103(1-2):47-52.
[NPL 3] Dreyfus et al., Science. 2012 Sep. 14; 337(6100): 1343-8. doi: 10.1126/science.1222908. Epub 2012 Aug. 9.

SUMMARY OF INVENTION

Technical Problem

In the current study, three HuMAbs were prepared that broadly reacted to the HA protein in influenza B virus. Three HuMAbs designated 5A7, 3A2, and 10C4 against influenza B virus were prepared using peripheral lymphocytes from vaccinated volunteers. In vitro, HuMAb 5A7 broadly neutralized influenza B strains isolated from 1985 to 2006, whereas 3A2 and 10C4 reacted to the Yamagata lineage only. Epitope mapping revealed that 3A2 and 10C4 recognized the 190-helix region near the receptor binding site in the hemagglutinin (HA) protein. Amino acid residues of the 190-helix readily mutate. 5A7 recognized amino acid positions 315 to 324 near the C terminal of HA1, a highly conserved region in influenza B viruses. Moreover, 5A7 showed therapeutic efficacy in mice even if HuMAb was injected 72 hours post-infection. HuMAb 5A7 synthesized from full-length variable gene-transfected CHO-K1 cells also showed neutralizing activity against influenza B viruses. These results indicate that the antibodies of the invention, including 5A7, can be used as therapeutics against influenza B virus.

It is therefore a feature of the present invention to provide therapeutics including antibodies and antigen-binding fragments thereof capable of preventing, inhibiting, and treating an influenza B infection.

Another feature of the present invention is to provide methods for producing such therapeutics.

A further feature of the present invention is to provide therapeutics effective against a wide range of influenza B viral strains.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

Solution to Problem

To achieve these and other advantages, and in accordance with the purposes of the present invention, as embodied and broadly described herein, the present invention relates to an anti-human influenza virus monoclonal antibody or an antigen-binding fragment thereof having a neutralization activity against a human influenza B virus, wherein the monoclonal antibody can include a human monoclonal antibody and/or a humanized monoclonal antibody.

The present invention provides a method for producing an anti-human influenza B virus monoclonal antibody. The method can include producing a hybridoma by fusing a peripheral blood mononuclear cell (PBMC) from a human being, for example a patient and/or a vaccine in an influenza B virus infection with a fusion partner cell capable of efficient cell fusion. The method can also include obtaining an anti-human influenza virus monoclonal antibody from the hybridoma. The influenza B virus in the method can include at least one of a B/Florida/4/2006 strain, a B/Shanghai/361/2002/ strain, a B/Johannesburg/5/1999 strain, a B/Yamanashi/166/ 1998 strain, a B/Mie/1/1993 strain, a B/Malaysia/2506/04 strain, a B/Shandong/7/1997 strain, and B/Victoria/2/1987 strain. The fusion partner cell is a SPYMEG cell. Thus, an anti-human influenza virus monoclonal antibody produced by the method is further provided.

The present invention provides a method of inhibiting or treating a human influenza B infection in a human subject including administering a therapeutically effective amount of the anti-human influenza B virus human antibody or antigen-binding fragment thereof of the invention to the human subject. The method can further include diagnosing the patient with an influenza B infection. The method can further include monitoring for a decrease in at least one symptom of an influenza B infection.

The present invention provides use of an anti-human influenza B virus monoclonal antibody or antigen-binding fragment thereof of the present invention to manufacture a medicament for inhibiting or treating a human influenza B infection in a human subject. The present invention also provides a method of detecting human influenza B in a human subject including contacting a sample from the human subject with an anti-human influenza B virus monoclonal antibody or antigen-binding fragment thereof of the invention. The present invention further provides a pharmaceutical composition containing an anti-human influenza virus monoclonal antibody or antigen-binding fragment thereof of the present invention and a pharmacologically acceptable carrier. The present invention still further provides a kit for at least one of the prevention, the treatment, and the detection of human influenza B in a human subject containing an anti-human influenza virus monoclonal antibody or antigen-binding fragment thereof of the present invention. The kit can include the pharmaceutical composition and/or one or more additional influenza B or other antagonists.

The accompanying drawings, which are incorporated in and constitute a part of this application, illustrate some of the embodiments of the present invention and together with the description, serve to explain the principles of the present invention.

BRIEF DESCRIPTION OF DRAWINGS

FIG. 1 shows the sequences of escape mutants selected by the incubation of B/Florida/4/2006 with HuMAbs. The amino acid sequences of the HA protein in the escape mutants are compared with the original B/Florida/4/2006. Asterisks indicate the amino acid residues different between the original virus and the escape mutants.

FIG. 3 shows expression plasmids bearing chimeric HA protein prepared with B/Shanghai/361/2002 (Sh/02) and B/Florida/4/2006 (Flo/06). 293T cells expressing the chimeric protein were subjected to an immunofluorescence assay (IFA) with 3A2 (left panels). White bars represent the amino acid sequence in Sh/02, and black bars represent the amino acid sequence in Flo/06. The different amino acid residues in the HA protein from each of the two viral strains are shown in the top and bottom bars.

Figure 2:
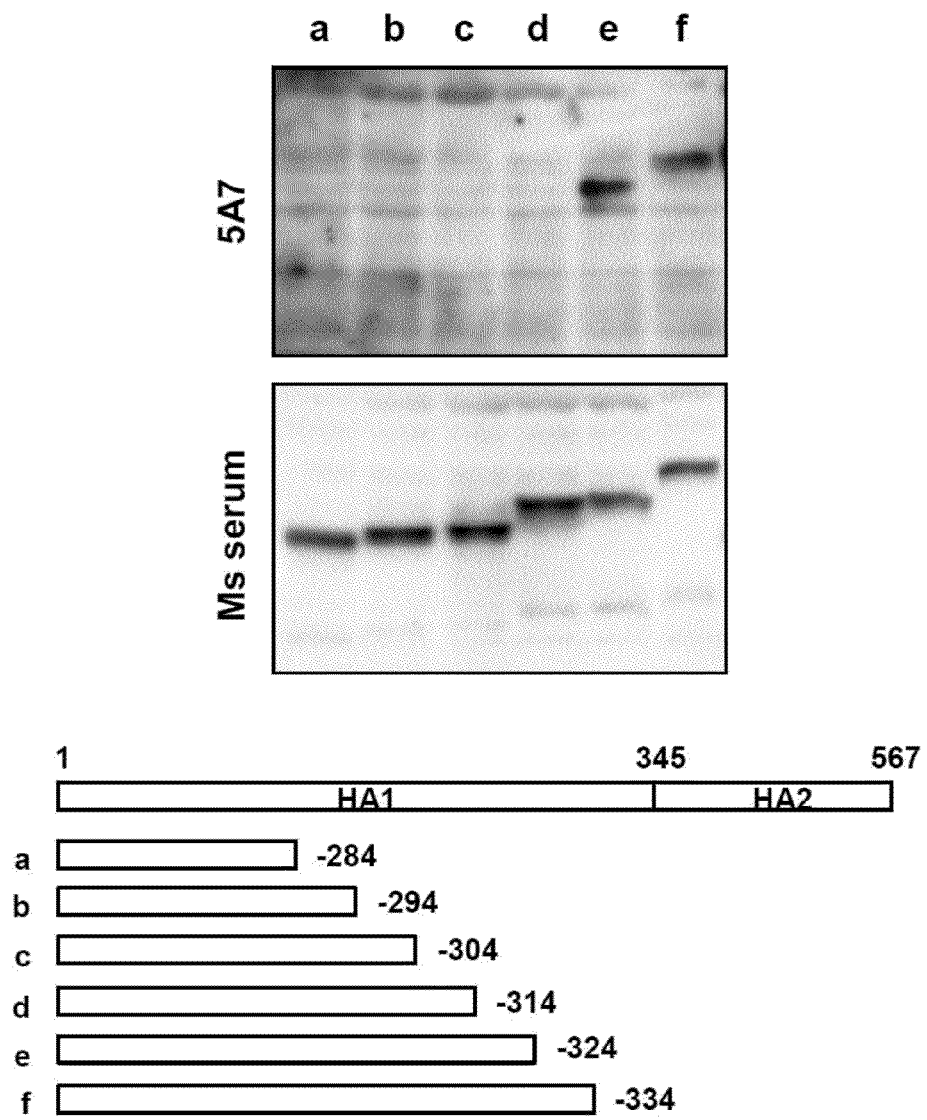
FIG. 2 shows a series of truncated forms of HA (a to 0 in an expression plasmid, which were prepared as depicted in the diagram. Transfected 293T cells were subjected to Western blotting with 5A7. The serum from a mouse infected with B/Ibaraki/2/1985 was used as a control (Ms serum).

CHO; solid lines) and compared with infectivity in the presence of 5A7 from hybridoma supernatant (5A7/hybridoma; dashed lines). HuMAbs (100 mcg/ml (microgram/nil)) were serially diluted four-fold.

FIG. 11 shows sequences of the $V_H$ and $V_L$ region of the three HuMAbs. These three HuMAbs were derived from different germ lines except D region $V_H$ of 3A2 and 10C4.

FIG. 12 shows sequences of the $V_H$ and $V_L$ region of the three HuMAbs. These three HuMAbs were derived from different germ lines except D region $V_H$ of 3A2 and 10C4.

FIG. 13 shows sequences of the $V_H$ and $V_L$ region of the three HuMAbs. These three HuMAbs were derived from different germ lines except D region $V_H$ of 3A2 and 10C4. The accompanying drawings, which are incorporated into and constitute a part of the specification, illustrate specific features/embodiments of the present invention, and taken in conjunction with the detailed description, serve to explain the principles of the present invention. It is to be understood that both the foregoing general description and the following detailed description are exemplary and explanatory only and are intended to provide a further explanation of the present invention, as claimed.

DESCRIPTION OF EMBODIMENTS

Detailed Description of the Present Invention

The present invention provides an anti-human influenza virus monoclonal antibody or an antigen-binding fragment thereof having a neutralization activity against a human influenza B virus, wherein the monoclonal antibody includes a human monoclonal antibody and/or a humanized monoclonal antibody. The monoclonal antibody or antigen-binding fragment thereof can have a neutralization activity against at least a B/Florida/4/2006 strain, a B/Shanghai/361/2002 strain, a B/Johannesburg/5/1999 strain, a B/Yamanashi/166/1998 strain, and a B/Mie/1/1993 strain. The monoclonal antibody or antigen-binding fragment thereof can have a neutralization activity against at least a B/Florida/4/2006 strain, a B/Shanghai/361/2002 strain, a B/Johannesburg/5/1999 strain, a B/Yamanashi/166/1998 strain, a B/Mie/1/1993 strain, a B/Malaysia/2506/04 strain, a B/Shandong/7/1997 strain, and a B/Victoria/2/1987 strain. The anti-human influenza B virus monoclonal antibody or antigen-binding fragment thereof can include an IgG, a Fab, a Fab', a F(ab')2, a scFv, a dsFv, or any combination thereof.

The anti-human influenza virus monoclonal antibody or antigen-binding fragment thereof can include at least one heavy chain variable region and/or at least one light chain variable region. The heavy chain variable region can include at least one of a first complementarity determining region (CDR1), a second complementarity determining region (CDR2), and a third complementarity determining region (CDR3). The CDR1 of the heavy chain variable region can have a first amino acid sequence including SEQ ID NO: 1, 7, or 13. The CDR2 of the heavy chain variable region can have a second amino acid sequence including SEQ ID NO: 2, 8, or 14. The CDR3 of the heavy chain variable region can have a third amino acid sequence including SEQ ID NO: 3, 9, or 15. The light chain variable region can also include at least one of a first complementarity determining region (CDR1), a second complementarity determining region (CDR2), and a third complementarity determining region (CDR3). The CDR1 of the light chain variable region can have a fourth amino acid sequence including SEQ ID NO: 4, 10, or 16. The CDR2 of the light chain variable region can have a fifth amino acid sequence including SEQ ID NO: 5, 11, or 17. The CDR3 of the light chain variable region can have a sixth amino acid sequence including SEQ ID NO: 6, 12, or 18.

The anti-human influenza virus monoclonal antibody or antigen-binding fragment can have the first amino acid sequence include SEQ ID NO: 1, the second amino acid sequence include SEQ ID NO: 2, the third amino acid sequence include SEQ ID NO: 3, the fourth amino acid sequence include SEQ ID NO: 4, the fifth amino acid sequence include SEQ ID NO: 5, and the sixth amino acid sequence include SEQ ID NO: 6. For example, the anti-human influenza virus monoclonal antibody can include antibody 5A7. The anti-human influenza virus monoclonal antibody or antigen-binding fragment thereof can have the first amino acid sequence include SEQ ID NO: 7, the second amino acid sequence include SEQ ID NO: 8, the third amino acid sequence include SEQ ID NO: 9, the fourth amino acid sequence include SEQ ID NO: 10, the fifth amino acid sequence include SEQ ID NO: 11 and the sixth amino acid sequence include SEQ ID NO: 12. For example, the anti-human influenza virus monoclonal antibody can include antibody 3A2. The anti-human influenza virus monoclonal antibody or antigen-binding fragment thereof can have the first amino acid sequence include SEQ ID NO: 13, the second amino acid sequence include SEQ ID NO: 14, the third amino acid sequence include SEQ ID NO: 15, the fourth amino acid sequence include SEQ ID NO: 16, the fifth amino acid sequence include SEQ ID NO: 17, and the sixth amino acid sequence include SEQ ID NO: 18. For example, the anti-human influenza virus monoclonal antibody can include antibody 10C4.

The monoclonal antibody can be produced by a hybridoma made by fusing a peripheral blood mononuclear cell (PBMC) from a human being, for example a patient and/or a vaccine having an influenza B virus infection with a fusion partner cell capable of efficient cell fusion. The influenza B virus of the infection can include at least one of a B/Florida/4/2006 strain, a B/Shanghai/361/2002 strain, a B/Johannesburg/5/1999 strain, a B/Yamanashi/166/1998 strain, a B/Mie/1/1993 strain, a B/Malaysia/2506/04 strain, a B/Shandong/7/1997 strain, and a B/Victoria/2/1987 strain. The fusion partner cell can be a SPYMEG cell.

Accordingly, the present invention provides a method for producing an anti-human influenza B virus monoclonal antibody. The method can include producing a hybridoma by fusing a peripheral blood mononuclear cell (PBMC) from a human being, for example a patient and/or a vaccine in an influenza B virus infection with a fusion partner cell capable of efficient cell fusion. The method can also include obtaining an anti-human influenza virus monoclonal antibody from the hybridoma. The influenza B virus in the method can include at least one of a B/Florida/4/2006 strain, a B/Shanghai/361/2002 strain, a B/Johannesburg/5/1999 strain, a B/Yamanashi/166/1998 strain, a B/Mie/1/1993 strain, a B/Malaysia/2506/04 strain, a B/Shandong/7/1997 strain, and B/Victoria/2/1987 strain. The fusion partner cell can be a SPYMEG cell. Thus, an anti-human influenza virus monoclonal antibody produced by the method is further provided. The monoclonal antibody can include, for example, a human monoclonal antibody and/or a humanized monoclonal antibody.

Anti-influenza antibodies and polypeptides containing antigen binding fragments thereof are provided as well as methods, uses, compositions, and kits employing the same. A method of forming an antibody specific to an influenza or a polypeptide or a fragment thereof is provided. Such a method can contain providing a nucleic acid encoding a influenza antigen polypeptide or a polypeptide containing an immunologically specific epitope thereof; expressing the polypeptide containing the antigen amino acid sequence or a polypeptide containing an immunologically specific epitope thereof from the isolated nucleic acid; and generating an antibody specific to the polypeptide obtained or a polypeptide containing an antigen binding fragment thereof. An antibody or polypeptide containing an antigen binding fragment thereof produced by the aforementioned method is provided. An isolated antibody or isolated polypeptide containing an antigen binding fragment thereof that specifically binds an influenza antigen is provided. Such an antibody can be generated using any acceptable method(s) known in the art. The antibodies as well as kits, methods, and/or other aspects of the present invention employing antibodies can include one or more of the following: a polyclonal antibody, a monoclonal antibody, a chimeric antibody, a single-chain antibody, a monovalent antibody, a diabody, and/or a humanized antibody.

Naturally occurring antibody structural units typically contain a tetramer. Each such tetramer can be composed of two identical pairs of polypeptide chains, each pair having one full-length light" (for example, about 25 kDa) and one full-length "heavy" chain (for example, about 50-70 kDa). The amino-terminal portion of each chain typically includes a variable region of about 100 to 110 or more amino acids that typically is responsible for antigen recognition. The carboxy-terminal portion of each chain typically defines a constant region that may be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. In light and heavy chains, the variable and constant regions can be joined by a "J" region of about 12 or more amino acids, with the heavy chain also including a "D" region of about 10 or more amino acids. See, e.g., Fundamental Immunology Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically contain the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. MoI. Biol. 196:901-917 (1987); Chothia et al., Nature 342:878-883 (1989).

"Antibody fragments" include a portion of an intact antibody, such as the antigen binding or variable region of the intact antibody. Examples of antibody fragments include Fab, Fab 1, F(ab')2, and Fv fragments; diabodies; linear antibodies (Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen-combining sites and is still capable of cross-linking antigen. "Fv" is an antibody fragment which contains a complete antigen-recognition and -binding site. This region includes a dimer of one heavy- and one light-chain variable domain in tight, non-covalent association. A single variable domain (or half of an Fv containing only three CDRs specific for an antigen) can recognize and bind an antigen. "Single-chain Fv" or "sFv" antibody fragments include the $V_H$ and $V_L$ domains of the antibody, wherein these domains are present in a single polypeptide chain. The Fv polypeptide can further contain a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Antibodies can be used as probes, therapeutic treatments and other uses. Antibodies can be made by injecting mice, rabbits, goats, or other animals with the translated product or synthetic peptide fragments thereof. These antibodies are useful in diagnostic assays or as an active ingredient in a pharmaceutical composition.

The antibody or polypeptide administered can be conjugated to a functional agent to form an immunoconguate. The functional agent can be a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate), an antibiotic, a nucleolytic enzyme, or any combination thereof. Chemotherapeutic agents can be used in the generation of immunoconjugates, e.g., methotrexate, adriamicin, vinca alkaloids (vincristine, vinblastine, etoposide), doxorubicin, melphalan, mitomycin C, chlorambucil, daunorubicin or other intercalating agents, enzymes, and/or fragments thereof, such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Enzymatically active toxins and fragments thereof that can be used include, for example, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricotheeenes. Any appropriate radionucleotide or radioactive agent known in the art or are otherwise available can be used to produce radioconjugated antibodies.

Conjugates of the antibody and cytotoxic agent can be made using a variety of bifunctional protein-coupling agents such as N-succinimidyl-3-(2-pyridyldithiol)propionate (SPDP); iminothiolane (IT); bifunctional derivatives of imidoesters (such as dimethyl adipimidate HCL); active esters (such as disuccinimidyl suberate); aldehydes (such as glutareldehyde); bis-azido compounds (such as bis(p-azidobenzoyl) hexanediamine); bis-diazonium derivatives (such as bis-(p-diazo-niumbenzoyl)-ethylenediamine); diisocyanates (such as tolyene 2,6-diisocyanate); bis-active fluorine compounds (such as 1,5-difluoro-2,4-dinitrobenzene); maleimidocaproyl (MC); valine-citrulline, dipeptide site in protease cleavable linker (VC); 2-amino-5-ureido pentanoic acid PAB=p-aminobenzylcarbamoyl ("self immolative" portion of linker) (Citrulene); N-methyl-valine citrulline where the linker peptide bond has been modified to prevent its cleavage by cathepsin B (Me); maleimidocaproyl-polyethylene glycol, attached to antibody cysteines; N-Succinimidyl 4-(2-pyridylthio)pentanoate (SPP); and N-succinimidyl 4-(N-maleimidomethyl)cyclohexane-1 carboxylate (SMCC). For example, a ricin immunotoxin can be prepared as described in Vitetta et al., Science, 238: 1098 (1987). Carbon-14-labeled 1-isothiocyanatobenzyl-3-methyldiethylene triaminepentaacctic acid (MX-DTPA) is an exemplary chelating agent for conjugation of radionucleotide to the antibody, see WO 94/11026. The antibody can be conjugated to a "receptor" (such as streptavidin) for utilization in tumor pre-targeting wherein the antibody-receptor conjugate is administered to the subject, followed by removal of unbound conjugate from the circulation using a clearing agent and then administration of a "ligand" (e.g., avidin) that is conjugated to a cytotoxic agent (e.g., a radionucleotide).

The antibodies of the present invention can be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. See, e.g., U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, and phycoerythrin; an example of a luminescent material includes luminol; examples of bioluminescent materials include luciferin, and aequorin.

Antibodies useful in practicing the present invention can be prepared in laboratory animals or by recombinant DNA techniques using the following methods. Polyclonal antibodies can be raised in animals by multiple subcutaneous (sc) or intraperitoneal (ip) injections of the gene product molecule or fragment thereof in combination with an adjuvant such as Freund's adjuvant (complete or incomplete). To enhance immuno-genicity, it can be useful to first conjugate the gene product molecule or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl, etc. Alternatively, immunogenic conjugates can be produced recombinantly as fusion proteins.

Animals can be immunized against the immunogenic conjugates or derivatives (such as a fragment containing the target amino acid sequence) by combining about 1 mg or about 1 microgram of conjugate (for rabbits or mice, respectively) with about 3 volumes of Freund's complete adjuvant and injecting the solution intradermally at multiple sites. Approximately 7 to 14 days later, animals are bled and the serum is assayed for antibody titer. Animals are boosted with antigen repeatedly until the titer plateaus. The animal can be boosted with the same molecule or fragment thereof as was used for the initial immunization, but conjugated to a different protein and/or through a different cross-linking agent. In addition, aggregating agents such as alum can be used in the injections to enhance the immune response.

The antibody administered can include a chimeric antibody. The antibody administered can include a humanized antibody. The antibody administered can include a completely humanized antibody. The antibodies can be humanized or partially humanized. Non-human antibodies can be humanized using any applicable method known in the art. A humanized antibody can be produced using a transgenic animal whose immune system has been partly or fully humanized. Any antibody or fragment thereof of the present invention can be partially or fully humanized. Chimeric antibodies can be produced using any known technique in the art. See, e.g., U.S. Pat. Nos. 5,169,939; 5,750,078; 6,020,153; 6,420,113; 6,423,511; 6,632,927; and 6,800,738.

The antibody administered can include a monoclonal antibody, that is, the anti-influenza antibodies of the present invention that can be monoclonal antibodies. Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro. Monoclonal antibodies can be screened as are described, for example, in Harlow & Lane, Antibodies, A Laboratory Manual, Cold Spring Harbor Press, New York (1988); Goding, Monoclonal Antibodies, Principles and Practice (2d ed.) Academic Press, New York (1986). Monoclonal antibodies can be tested for specific immunoreactivity with a translated product and lack of immunoreactivity to the corresponding prototypical gene product.

Monoclonal antibodies can be prepared by recovering spleen cells from immunized animals and immortalizing the cells in conventional fashion, e.g., by fusion with myeloma cells. The clones are then screened for those expressing the desired antibody. The monoclonal antibody preferably does not cross-react with other gene products. After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal. The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the present invention can be readily isolated and sequenced using conventional procedures (e.g., by using oligonucleotide probes that are capable of binding specifically to genes encoding the heavy and light chains of murine antibodies). The hybridoma cells of the present invention can serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences or by covalently joining to the immunoglobulin coding sequence all or part of the coding sequence for a non-immunoglobulin polypeptide. Such a non-immunoglobulin polypeptide can be substituted for the constant domains of an antibody of the present invention, or can be substituted for the variable domains of one antigen-combining site of an antibody of the invention to create a chimeric bivalent antibody. Preparation of antibodies using recombinant DNA methods such as the phagemid display method, can be accomplished using commercially available kits, as for example, the Recombinant Phagemid Antibody System available from Pharmacia (Uppsala, Sweden), or the SurfZAP™ phage display system (Stratagene Inc., La Jolla, Calif.).

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The antibodies can be diabodies. The term "diabodies' refers to small antibody fragments with two antigen-binding sites, which fragments include a heavy-chain variable domain ($V_H$) connected to a light-chain variable domain ($V_L$) in the same polypeptide chain (Vn-$V_L$). By using a linker that is too short to allow pairing between the two domains on the same chain, the domains can be forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The antibody administered can include a single-chain antibody. The antibodies can be monovalent antibodies. Methods for preparing monovalent antibodies are well known in the art. For example, one method involves recombinant expression of immunoglobulin light chain and modified heavy chain. The heavy chain can be truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

The antibodies can be bispecific. Bispecific antibodies that specifically bind to one protein and that specifically bind to other antigens relevant to pathology and/or treatment are produced, isolated, and tested using standard procedures that have been described in the literature. [See, e.g., Pluckthun & Pack, Immunotechnology, 3:83-105 (1997); Carter, et al., J. Hematotherapy, 4:463-470 (1995); Renner & Pfreundschuh, Immunological Reviews, 1995, No. 145, pp. 179-209; Pfreundschuh U.S. Pat. No. 5,643,759; Segal, et al., J. Hematotherapy, 4:377-382 (1995); Segal, et al., Immunobiology, 185:390-402 (1992); and Bolhuis, et al., Cancer Immunol. Immunother., 34:1-8 (1991)].

The antibodies disclosed herein can be formulated as immunoliposomes. Liposomes containing the antibody are prepared by methods known in the art. such as described in Epstein et al., Proc. Natl. Acad. Sci. USA, 82: 3688 (1985); Hwang et al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse-phase evaporation method with a lipid composition containing phosphatidylcholine, cholesterol, and PEG-derivatized phosphatidylethanolamine (PEG-PE). Liposomes can be extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction. A chemotherapeutic agent (such as Doxorubicin) is optionally contained within the liposome. See Gabizon et al, J. National Cancer Inst., 81(19): 1484 (1989).

The influenza antagonist can include an aptamer that binds the hemagglutinin (HA) protein of an influenza B virus. The aptamer can bind HA in the same location/epitope as the antibodies described herein and/or to other locations/epitopes. The aptamer can contain one or more of a nucleic acid, a RNA, a DNA, and an amino acid. Aptamers can be selected and produced using any suitable technique or protocol. For example, oligonucleotide libraries with variable regions ranging from 18 to 50 nucleotides in length can be used as templates for run-off transcription reactions to generate random pools of RNA aptamers. This aptamer pool can then be exposed to unconjugated matrix to remove non-specific interacting species. The remaining pool is then incubated with an immobilized target. The majority of aptamer species in this pool can have low affinity, for the target can be washed away leaving a smaller, more specific pool bound to the matrix. This pool can then be eluted, precipitated, reverse transcribed, and used as a template for run-off transcription. After five rounds of selection, aliquots can be removed that are cloned and sequenced. Selection can be continued until similar sequences are reproducibly recovered.

Aptamer production can be performed using a bead-based selection system. In this process, a library of beads is generated in which each bead is coated with a population of aptamers with identical sequences composed of natural and modified nucleotides. This bead library, which can contain greater than 100,000,000 unique sequences, can be incubated with a peptide that corresponds to hemagglutinin (HA) protein, or a portion thereof, e.g., an extracellular domain, that is conjugated with a tag such as a fluorescent dye. After washing, beads that demonstrate the highest binding affinity can be isolated and aptamer sequences can be determined for subsequent synthesis.

The present invention provides a method of inhibiting or treating a human influenza B infection in a human subject including administering a therapeutically effective amount of the anti-human influenza B virus monoclonal antibody or antigen-binding fragment thereof of the invention to the human subject. The method can further include diagnosing the patient with an influenza B infection. Anti-influenza antibodies or antigen-binding fragment thereof of the present invention can be administered to a subject before, during, and/or after diagnosing the patient as having an influenza infection.

The method can further include monitoring for a decrease in at least one symptom of an influenza B infection. For example, the at least one symptom can include fever, headache, fatigue, chills, malaise, myalgia, arthralgia, nasal congestion, sore throat, cough, respiratory distress, stomach pain, or any combination thereof. The anti-human influenza virus monoclonal antibody or antigen-binding administered in combination with one or more additional therapies directed to influenza B and/or other influenzas such as influenza A and/or influenza C. The combination can act synergistically to inhibit or treat the influenza B infection. The one or more additional therapies can include, for example, a neuraminidase inhibitor, a hemagglutinin inhibitor, an anti-inflammatory agent, or any combination thereof. The neuraminidase inhibitor can include, for example, zanamivir, oseltamivir, peramivir, laninamivir, any pharmaceutically acceptable salt thereof, or any combination thereof.

In accordance with the present invention, two or more influenza antagonists can be administered. At least one of the influenza antagonists can include an influenza B antagonist. The at least one influenza B antagonist can be combined with one or more influenza A antagonists and/or one or more influenza C antagonists. At least one influenza antagonist can be administered in combination with one or more additional therapies directed against an influenza viral infection. The administration of two or more therapies, including one or more influenza antagonists, can be simultaneous, sequential, or in combination. Accordingly, when two or more therapies are administered, they need not be administered simultaneously or in the same way or in the same dose. When administered simultaneously, the two or more therapies can be administered in the same composition or in different compositions. The two or more therapies can be administered using the same route of administration or different routes of administration. When administered at different times, the therapies can be administered before or after each other. Administration order of the two or more therapies can be alternated. The respective doses of the one or more therapies can be varied over time. The type of one or more therapy can be varied over time. When administered at separate times, the separation of the two or more administrations can be any time period. If administered multiple times, the length of the time period can vary. The separation between administration of the two or more two or more therapies can be 0 seconds, 1 second, 5 seconds, 10 seconds, 30 seconds, 1 minute, 5 minutes, 10 minutes, 15 minutes, 20 minutes, 30, minutes, 45 minutes, 1 hour, 1.5 hours, 2 hours, 2.5 hours, 3 hours, 4 hours, 5 hours, 7.5 hours, 10 hours, 12 hours, 15 hours, 18 hours, 21 hours, 24 hours, 1.5 days, 2 days, 3 days, 4 days, 5 days, 6 days, 7 days, 10 days, 2 weeks, 3 weeks, 4 weeks, one month, 6 weeks, 8 weeks, three months, six months, 1 year or longer.

Two or more influenza antagonists can act synergistically to treat or reduce an influenza infection or a symptom of the same, for example, fever. An influenza antagonist can be one or more anti-influenza antibody alone or in combination with one or more other influenza antagonist, for example, a small drug pharmaceutical, or other anti-influenza therapy. Two or more anti-influenza antibodies, or at least one anti-influenza antibody and one or more additional therapies can act synergistically to treat or reduce an influenza B viral infection. Two or more therapies, including one or more anti-influenza antibody, can be administered in synergistic amounts. Accordingly, the administration of two or more therapies can have a synergistic effect on the decrease in one or more symptoms of an influenza infection, whether administered simultaneously, sequentially, or in any combination. A first therapy can increase the efficacy of a second therapy greater than if second therapy was employed alone, or a second therapy increases the efficacy of a first therapy, or both. The effect of administering two or more therapies can be such that the effect on decreasing one or more symptoms of an influenza infection is greater than the additive effect of each being administered alone. When given in synergistic amounts, one therapy can enhance the efficacy of one or more other therapy on the decrease in one or more symptoms of an influenza infection, even if the amount of one or more therapy alone would have no substantial effect on one or more symptom of an influenza infection. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003) and/or by calculating the combination index (CI) using CalcuSyn software.

The present invention provides use of an anti-human influenza B virus monoclonal antibody or antigen-binding fragment thereof of the present invention to manufacture a medicament for inhibiting or treating a human influenza B infection in a human subject. The present invention also provides a method of detecting human influenza B in a human subject. The method can include contacting a sample from the human subject with an anti-human influenza B virus human antibody or antigen-binding fragment thereof of the invention. The method can further include detecting the presence or absence of a human influenza B virus in the human subject based on whether the antibody binds a hemagglutinin (HA) protein of the human influenza B virus. The present invention further provides a pharmaceutical composition containing an anti-human influenza virus human antibody or antigen-binding fragment thereof of the present invention and a pharmacologically acceptable carrier. The present invention still further provides a kit for at least one of the prevention, the treatment, and the detection of human influenza B in a human subject containing an anti-human influenza virus monoclonal antibody or antigen-binding fragment thereof of the present invention. The kit can include the pharmaceutical composition and/or one or more additional anti-influenza B or other antagonists.

Exact formulation, route of administration and dosage can be chosen by the individual physician in view of the patient's condition. [See, e.g., Fingl et. al., in The Pharmacological Basis of Therapeutics, 1975, Ch. 1 p. I.] The attending physician can determine when to terminate, interrupt, or adjust administration due to toxicity, or to organ dysfunctions. Conversely, the attending physician can also adjust treatment to higher levels if the clinical response were not adequate, precluding toxicity. The magnitude of an administrated dose in the management of disorder of interest will vary with the severity of the disorder to be treated and the route of administration. The severity of the disorder can, for example, be evaluated, in part, by standard prognostic evaluation methods. The dose and dose frequency, can vary according to the age, body weight, and response of the individual patient. A program comparable to that discussed above can be used in veterinary medicine.

Use of pharmaceutically acceptable carriers to formulate the compounds herein disclosed for the practice of the invention into dosages suitable for systemic administration is within the scope of the present invention. With proper choice of carrier and suitable manufacturing practice, the compositions relevant to the present invention, in particular, those formulated as solutions, can be administered parenterally, such as by intravenous injection. The compounds can be formulated readily using pharmaceutically acceptable carriers well known in the art into dosages suitable for oral administration. Such carriers enable the compounds relevant to the present invention to be formulated as tablets, pills, capsules, liquids, gels, syrups, slurries, tablets, dragees, solutions, suspensions and the like, for oral ingestion by a patient to be treated.

The therapeutic agent can be prepared in a depot form to allow for release into the body to which it is administered is controlled with respect to time and location within the body (see, for example, U.S. Pat. No. 4,450,150). Depot forms of therapeutic agents can be, for example, an implantable composition containing the therapeutic agent and a porous or non-porous material, such as a polymer, wherein the therapeutic agent is encapsulated by or diffused throughout the material and/or degradation of the non-porous material. The depot is then implanted into the desired location within the body and the therapeutic agent is released from the implant at a predetermined rate.

The therapeutic agent that is used in the present invention can be formed as a composition, such as a pharmaceutical composition containing a carrier and a therapeutic compound. Pharmaceutical compositions containing the therapeutic agent can include more than one therapeutic agent. The pharmaceutical composition can alternatively contain a therapeutic agent in combination with other pharmaceutically active agents or drugs.

The carrier can be any suitable carrier. For example, the carrier can be a pharmaceutically acceptable carrier. With respect to pharmaceutical compositions, the carrier can be any of those conventionally used with consideration of chemico-physical considerations, such as solubility and lack of reactivity with the active compound(s), and by the route of administration. In addition to, or in the alternative to, the following described pharmaceutical compositions, the therapeutic compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents; are well-known to those skilled in the art and are readily available to the public. The pharmaceutically acceptable carrier can be chemically inert to the active agent(s) and one which has no detrimental side effects or toxicity under the conditions of use. The choice of carrier can be determined in part by the particular therapeutic agent, as well as by the particular method used to administer the therapeutic compound. There are a variety of suitable formulations of the pharmaceutical composition of the present invention. The following formulations for oral, aerosol, parenteral, subcutaneous, transdermal, transmucosal, intestinal, intramedullary injections, direct intraventricular, intravenous, intranasal, intraocular, intramuscular, intraarterial, intrathecal, intraperitoneal, rectal, and vaginal administration are exemplary and are in no way limiting. More than one route can be used to administer the therapeutic agent, and in some instances, a particular route can provide a more immediate and more effective response than another route. Depending on the specific disorder being treated, such agents can be formulated and administered systemically or locally. Techniques for formulation and administration may be found in Remington's Pharmaceutical Sciences, 18th ed., Mack Publishing Co., Easton, Pa. (1990).

Formulations suitable for oral administration can include (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can contain the inhibitor in a flavor, usually sucrose and acacia or tragacanth, as well as pastilles containing the inhibitor in an inert base, such as gelatin and glycerin, or sucrose and acacia, emulsions, gels, and the like containing, in addition to, such excipients as are known in the art.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers can be added.

The therapeutic agent, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressurized preparations, such as in a nebulizer or an atomizer. Such spray formulations also may be used to spray mucosa. Topical formulations are well known to those of skill in the art. Such formulations are particularly suitable in the context of the invention for application to the skin.

Injectable formulations are in accordance with the present invention. The parameters for effective pharmaceutical carriers for injectable compositions are well-known to those of ordinary skill in the art [see, e.g., Pharmaceutics and Pharmacy Practice, J. B. Lippincott Company, Philadelphia, Pa., Banker and Chalmers, eds., pages 238250 (1982), and ASHP Handbook on Injectable Drugs, Toissel, 4th ed., pages 622 630 (1986)]. For injection, the agents of the present invention can be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Formulations suitable for parenteral administration can include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The therapeutic agent can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, poly(ethyleneglycol) 400, glycerol, dimethylsulfoxide, ketals such as 2,2-dimethyl-1,3-dioxolane-4-methanol, ethers, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethyl-cellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain from about 0.5% to about 25% by weight of the drug in solution. Preservatives and buffers can be used. In order to minimize or eliminate irritation at the site of injection, such compositions may contain one or more nonionic surfactants having a hydrophilic-lipophilic balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The therapeutic agent can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

Agents intended to be administered intracellularly may be administered using techniques well known to those of ordinary skill in the art. For example, such agents can be encapsulated into liposomes. Liposomes are spherical lipid bilayers with aqueous interiors. Molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly. Materials and methods described for one aspect of the present invention can also be employed in other aspects of the present invention. For example, a material such a nucleic acid or antibody described for use in screening assays can also be employed as therapeutic agents and vice versa.

The present invention includes the following aspects/embodiments/features in any order and/or in any combination:

1. The present invention relates to an anti-human influenza virus monoclonal antibody or an antigen-binding fragment thereof comprising a neutralization activity against a human influenza B virus, wherein the monoclonal antibody comprises a human monoclonal antibody or a humanized monoclonal antibody.

2. The anti-human influenza virus monoclonal antibody or antigen-binding fragment thereof of any preceding or following embodiment/feature/aspect, wherein the monoclonal antibody or antigen-binding fragment thereof has a neutralization activity against at least a B/Florida/4/2006 strain, a B/Shanghai/361/2002 strain, a B/Johannesburg/5/1999 strain, a B/Yamanashi/166/1998 strain, and a B/Mie/1/1993 strain.

3. The anti-human influenza virus monoclonal antibody or antigen-binding fragment thereof of any preceding or following embodiment/feature/aspect, wherein the monoclonal antibody or antigen-binding fragment thereof has a neutralization activity against at least a B/Florida/4/2006 strain, a B/Shanghai/361/2002 strain, a B/Johannesburg/5/1999 strain, a B/Yamanashi/166/1998 strain, a B/Mie/1/1993 strain, a B/Malaysia/2506/04 strain, a B/Shandong/7/1997 strain, and a B/Victoria/2/1987 strain.

4. The anti-human influenza virus human monoclonal antibody of any preceding or following embodiment/feature/aspect, wherein the human monoclonal antibody is produced by a hybridoma made by fusing a peripheral blood mononuclear cell (PBMC) from a human being having an influenza B virus infection with a fusion partner cell capable of efficient cell fusion.

5. The anti-human influenza virus human monoclonal antibody of any preceding or following embodiment/feature/aspect, wherein the influenza B virus comprises at least one of a B/Florida/4/2006 strain, a B/Shanghai/361/2002 strain, a B/Johannesburg/5/1999 strain, a B/Yamanashi/166/1998 strain, a B/Mie/1/1993 strain, a B/Malaysia/2506/04 strain, a B/Shandong/7/1997 strain, and a B/Victoria/2/1987 strain.

6. The anti-human influenza B virus human monoclonal antibody of any preceding or following embodiment/feature/aspect, wherein the fusion partner cell is a SPYMEG cell.

7. The anti-human influenza B virus monoclonal antibody or antigen-binding fragment thereof of any preceding or following embodiment/feature/aspect comprising an IgG, a Fab, a Fab', a F(ab')2, a scFv, or a dsFv.

8. The anti-human influenza virus monoclonal antibody or antigen-binding fragment thereof of any preceding or following embodiment/feature/aspect, comprising:
a heavy chain variable region comprising
a first complementarity determining region (CDR1) having a first amino acid sequence comprising SEQ ID NO: 1, 7, or 13,
a second complementarity determining region (CDR2) having a second amino acid sequence comprising SEQ ID NO: 2, 8, or 14, and
a third complementarity determining region (CDR3) having a third amino acid sequence comprising SEQ ID NO: 3, 9, or 15, and
a light chain variable region comprising
a first complementarity determining region (CDR1) having a fourth amino acid sequence comprising SEQ ID NO: 4, 10, or 16;

a second complementarity determining region (CDR2) having a fifth amino acid sequence comprising SEQ ID NO: 5, 11, or 17, and
a third complementarity determining region (CDR3) having a sixth amino acid sequence comprising SEQ ID NO: 6, 12, or 18.

9. The anti-human influenza virus monoclonal antibody or antigen-binding fragment thereof of any preceding or following embodiment/feature/aspect, wherein the first amino acid sequence comprises SEQ ID NO: 1, the second amino acid sequence comprises SEQ ID NO: 2, the third amino acid sequence comprises SEQ ID NO: 3, the fourth amino acid sequence comprises SEQ ID NO: 4, the fifth amino acid sequence comprises SEQ ID NO: 5, and the sixth amino acid sequence comprises SEQ ID NO: 6.

10. The anti-human influenza virus monoclonal antibody or antigen-binding fragment thereof of any preceding or following embodiment/feature/aspect, wherein the anti-human influenza virus monoclonal antibody comprises antibody 5A7.

11. The anti-human influenza virus monoclonal antibody or antigen-binding fragment thereof of any preceding or following embodiment/feature/aspect, wherein the first amino acid sequence comprises SEQ ID NO: 7, the second amino acid sequence comprises SEQ ID NO: 8, the third amino acid sequence comprises SEQ ID NO: 9, the fourth amino acid sequence comprises SEQ ID NO: 10, the fifth amino acid sequence comprises SEQ ID NO: 11, and the sixth amino acid sequence comprises SEQ ID NO: 12.

12. The anti-human influenza virus monoclonal antibody or antigen-binding fragment thereof of any preceding or following embodiment/feature/aspect, wherein the anti-human influenza virus monoclonal antibody comprises antibody 3A2.

13. The anti-human influenza virus monoclonal antibody or antigen-binding fragment thereof of any preceding or following embodiment/feature/aspect, wherein the first amino acid sequence comprises SEQ ID NO: 13, the second amino acid sequence comprises SEQ ID NO: 14, the third amino acid sequence comprises SEQ ID NO: 15, the fourth amino acid sequence comprises SEQ ID NO: 16, the fifth amino acid sequence comprises SEQ ID NO: 17, and the sixth amino acid sequence comprises SEQ ID NO: 18.

14. The anti-human influenza virus monoclonal antibody or antigen-binding fragment thereof of any preceding or following embodiment/feature/aspect, wherein the anti-human influenza virus monoclonal antibody comprises antibody 10C4.

15. A pharmaceutical composition comprising the anti-human influenza virus human monoclonal antibody or antigen-binding fragment thereof of any preceding or following embodiment/feature/aspect and a pharmacologically acceptable carrier.

16. A kit for at least one of the prevention, the treatment, and the detection of human influenza B in a human subject comprising the anti-human influenza virus human monoclonal antibody or antigen-binding fragment thereof of any preceding or following embodiment/feature/aspect.

17. A method of inhibiting or treating a human influenza B infection in a human subject comprising administering a therapeutically effective amount of the anti-human influenza B virus monoclonal antibody or antigen-binding fragment thereof of any preceding or following embodiment/feature/aspect to the human subject.

18. The method of inhibiting or treating a human influenza B infection in a human subject of any preceding or following embodiment/feature/aspect, further comprising diagnosing the patient with an influenza B infection.

19. The method of inhibiting or treating a human influenza B infection in a human subject of any preceding or following embodiment/feature/aspect, further comprising monitoring for a decrease in at least one symptom of an influenza B infection.

20. The method of inhibiting or treating a human influenza B infection in a human subject of any preceding or following embodiment/feature/aspect, wherein the at least one symptom comprises fever, headache, fatigue, chills, malaise, myalgia, arthralgia, nasal congestion, sore throat, cough, respiratory distress, or stomach pain, or any combination thereof.

21. The method of inhibiting or treating a human influenza B infection in a human subject of any preceding or following embodiment/feature/aspect, wherein the anti-human influenza virus human monoclonal antibody or antigen-binding fragment thereof of claim 1 is administered in combination with one or more additional therapies directed to influenza B.

22. The method of inhibiting or treating a human influenza B infection in a human subject of any preceding or following embodiment/feature/aspect, wherein the combination acts synergistically to inhibit or treat the influenza B infection.

23. The method of inhibiting or treating a human influenza B infection in a human subject of any preceding or following embodiment/feature/aspect, wherein the one or more additional therapies comprise a neuraminidase inhibitor, a hemagglutinin inhibitor, an anti-inflammatory agent, or any combination thereof.

24. The method of inhibiting or treating a human influenza B infection in a human subject of any preceding or following embodiment/feature/aspect, wherein the neuraminidase inhibitor comprises zanamivir, oseltamivir, peramivir, laninamivir, any pharmaceutically acceptable salt thereof, or any combination thereof.

25. Use of the anti-human influenza B virus human monoclonal antibody or antigen-binding fragment thereof of any preceding or following embodiment/feature/aspect to manufacture a medicament for inhibiting or treating a human influenza B infection in a human subject.

26. A method of detecting human influenza B in a human subject comprising; contacting a sample from the human subject with the anti-human influenza B virus antibody or antigen-binding fragment thereof of any preceding or following embodiment/feature/aspect; and
detecting the presence or absence of a human influenza B virus in the human subject based on whether the antibody binds a hemagglutinin (HA) protein of the human influenza B virus.

27. A method for producing an anti-human influenza B virus human monoclonal antibody comprising:
producing a hybridoma by fusing a peripheral blood mononuclear cell (PBMC) from a human being having an influenza B virus infection with a fusion partner cell capable of efficient cell fusion; and
obtaining an anti-human influenza virus monoclonal antibody from the hybridoma.

28. The method for producing an anti-human influenza B virus human monoclonal antibody of any preceding or following embodiment/feature/aspect, wherein the influenza B virus comprises at least one of a B/Florida/4/2006 strain, a B/Shanghai/361/2002 strain, a B/Johannesburg/5/1999 strain, a B/Yamanashi/166/1998 strain, a B/Mie/1/1993 strain, a B/Malaysia/2506/04 strain, a B/Shandong/7/1997 strain, and B/Victoria/2/1987 strain.

29. The method for producing an anti-human influenza virus human monoclonal antibody of any preceding or following embodiment/feature/aspect, wherein the fusion partner cell is a SPYMEG cell.

30. An anti-human influenza virus human monoclonal antibody produced by the method of any preceding or following embodiment/feature/aspect.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be exemplary of, but not limiting, the present invention. Human materials were collected using protocols approved by the Institutional Review Boards of the Research Institute for Microbial Diseases, Osaka University (#19-8-6). Animal studies were conducted under the applicable laws and guidelines for the care and use of laboratory animals in the Research Institute for Microbial Diseases, Osaka University. They were approved by the Animal Experiment Committee of the Research Institute for Microbial Diseases, Osaka University (#H21-24-0), as specified in the Fundamental Guidelines for the Proper Conduct of Animal Experiment and Related Activities in Academic Research Institutions under the jurisdiction of the Ministry of Education, Culture, Sports, Science and Technology, Japan, 2006. The National Institute of Infectious Diseases and Dr. Shin-ichi Tamura (the National Institute of Infectious Diseases) provided viral strains. Natsuko Fukura, Azusa Asai, Tadahiro Sasaki, and Yohei Watanabe provided helpful advice and technical assistance. Data are expressed as the means+ or −standard errors of the means (SEM). Statistical analysis was performed by Student's t test. A P value of <0.05 was considered significant.

Eight influenza B vaccine strains (B/Victoria/2/1987, B/Mie/1/1993, B/Shandong/7/1997, B/Yamanashi/166/1998, B/Johannesburg/5/1999, B/Shanghai/361/2002, B/Malaysia/2506/2004, and B/Florida/4/2006) and the mouse-adapted strain B/Ibaraki/2/1985 were used. The B/Malaysia/2506/2004 and B/Florida/4/2006 strains were kindly provided by the National Institute of Infectious Diseases, Tokyo, Japan. Mouse-adapted B/Ibaraki/2/1985 strain was provided by Dr. S. Tamura, National Institute of Infectious Diseases (Chen et al., Vaccine 19:1446-1455). Viruses were propagated either in Madin-Darby canine kidney (MDCK) cells or in 9-day-old embryonated chicken eggs. Infectivity was titrated by focus-forming assay.

EXAMPLES

The present invention will be further clarified by the following examples, which are intended to be exemplary of, but not limiting, the present invention.

Example 1

Human monoclonal antibodies (HuMAbs) were prepared in accordance with the procedure described in Kubota-Koketsu et al., Biochemical and Biophysical Research Communications 387:180-185 (2009). Healthy volunteers were vaccinated with the HA split vaccine including A/Brisbane/59/2007 (H1N1), A/Uruguay/716/2007 (H3N2), and B/Florida/4/2006 strains. One to two weeks later, the vaccine-derived PBMCs were fused with SPYMEG cells and after screening and cloning, three hybridoma clones producing HuMAbs, designated 5A7, 3A2, and 10C4, were established. The reactivity of the HuMAbs was tested by IFA and Western blotting.

Briefly, 10 ml blood was drawn from a healthy volunteer vaccinated in the 2008/2009 winter season with trivalent HA split vaccine, which included A/Brisbane/59/2007, A/Uruguay/716/2007, and B/Florida/4/2006 (The Research Foundation for Microbial Diseases of Osaka University, Kagawa, Japan), and then the PBMCs were collected by density gradient centrifugation through Ficoll-Paque Plus (GE Healthcare, Uppsala, Sweden). SPYMEG cells, established from mouse myeloma cell line SP2/0-Ag14 and human megakaryoblastic cell line MEG-01, were used as fusion partner cells. SPYMEG cells are non-secretors of human and murine immunoglobulin. The PBMCs were fused with SPYMEG cells using polyethylene glycol #1500 (Roche Diagnostics, Mannheim, Germany). The fused cells were cultured in Dulbecco's modified Eagle medium (DMEM; Invitrogen, Carlsbad, Calif.) supplemented with 15% fetal bovine serum and hypoxanthine-aminopterin-thymidine. The first screening for MAb specific for influenza viruses was performed by immunofluorescence assay (IFA). For the IFA, the infected cells were fixed with absolute ethanol and then reacted with hybridoma supernatant for 30 min at 37 deg C., followed by incubation with FITC-conjugated anti-human IgG for 45 min at 37 deg C. The cells in the specific MAb-positive wells were cloned by limiting dilution, then followed by a second screening by IFA. Hybridoma cells taken from IFA-positive wells that had a single colony per well were cultured and expanded in Hybridoma-SFM (Invitrogen). MAb was purified from 100 ml hybridoma culture supernatant by affinity chromatography using HiTrap Protein G HP Columns (GE Healthcare) and then dialyzed into phosphate buffered saline (PBS) using Slide-A-Lyzer® Dialysis Cassettes (Thermo Scientific, Waltham, Mass.).

For IgG isotyping, ELISA microplates (Maxsorp; Nunc, Copenhagen, Denmark) were coated overnight at 4 deg C. with goat anti-human IgG (Jackson ImmunoResearch Laboratories, Inc, West Grove, Pa.) in 0.05 M sodium bicarbonate buffer (pH 8.6). After washing with PBS including 0.1% Tween-20, the wells were blocked with 0.5% BSA in PBS for 1 hour at 37 deg C. After washing again, the wells were incubated with hybridoma supernatants or control serum for 2 hours at 37 deg C. Following further washing, the wells were incubated with HRP-conjugated anti-human IgG1, IgG2, IgG3, or IgG4 (SouthernBiotech, Birmingham, Ala.) for 1 hour at 37 deg C. The wells were washed five times followed by incubation with TMB peroxidase substrate (KPL, Gaithersburg, Md.) at room temperature in the dark. After 20 minutes, the reaction was stopped with 2N H2SO4 solution. The color development was read at 450 nm in an ELISA Photometer (Biotek ELISA Reader; Biotek, Winooski, Vt.). All samples were run in triplicate.

For the sequencing of HuMAb variable regions, total RNA extracted from the hybridoma using an RNeasy Mini Kit (Qiagen) was subjected to RT-PCR using a PrimeScript RT reagent Kit (Takara, Shiga, Japan) with an oligo (dT) primer. The coding region of the H- and L-chains of HuMAb was amplified by PCR with the following primers: 5'-ATG-GAGTTTGGGCTGAGCTGGGTT-3' (H-chain-forward) (SEQ ID NO. 19) and 5'-CTCCCGCGGCTTTGTCTTG-GCATTA-3' (H-chain-reverse) (SEQ ID NO. 20); and 5'-ATGGCCTGGRYCYCMYTCYWCCTM-3' (L-chain-forward) (SEQ ID NO. 21) and 5'-TGGCAGCTGTAGCT-TCTGTGGGACT-3' (L-chain-reverse) (SEQ ID NO. 22). PCR products were ligated into pGEM-T Easy Vector (Promega) and their sequences were analyzed using a BigDye Terminator v3.1 Cycle Sequencing Kit and an ABI Prism 3100 Genetic Analyzer (Applied Biosystems, Foster City, Calif.).

IgG plasmids were constructed using T Easy Vectors with the variable region gene of H- and L-chains were subjected to PCR to add restriction enzyme sites and a Kozak sequence with the following primer sets (restriction enzyme sites are underlined): 5'-ATTTGCGGCCGCCATG-GAGTTTGGGCTGAG-3' (HC_5Fw_NotI; H-chain-forward) (SEQ ID NO. 23) and 5'-ATACTCGAGGGTGC-CAGGGGGAAGACCGATG-3' (HC_Reverse_XhoI; H-chain-reverse) (SEQ ID NO. 24); and 5'-ATTTGCGGC-CGCCATGGCCTGGGCTCTGCT-3' (5A7Lambda_18 Fw_NotI; L-chain-forward) (SEQ ID NO. 25) and 5'-ATACTCGAGGGCGGGAACAGAGTGACCGTGG-3' (Lambda_Reverse_XhoI; L-chain-reverse) (SEQ ID NO. 26). PCR products of the coding region of H- and L-chains were digested by restriction enzymes, Not I and Xho I, and then ligated to expression vectors, pQCXIP-hCH and pQCXIH-hC lambda, which have a human immunoglobulin-constant region of gamma and lambda chains (MBL), respectively.

All of three HuMAbs reacted with the HA protein in influenza B virus (Table 1). HuMAbs, 5A7 and 10C4 were IgG1 isotype, and 3A2 was IgG3 (Table 1). Sequencing analysis of the $V_H$ and $V_L$ region of the three HuMAbs revealed that each had different amino acid residues in antigenic regions including the complementarity-determining regions (CDRs) (Tables 2 and 3).

TABLE 1

Table 1: Pattern of Reactivity of HuMAbs.

| | Target | Isotype | IFA | Reducing WB |
|---|---|---|---|---|
| 5A7 | HA of influenza B | IgG1 | +[1] | + |
| 3A2 | HA of influenza B | IgG3 | + | −[2] |
| 10C4 | HA of influenza B | IgG1 | + | − |

[1] Positive result
[2] Negative result

TABLE 2

Table 2: Deduced Amino Acid Sequences of CDRs in the $V_H$ of three HuMAbs.

| $V_H$ | CDR1 | SEQ. ID No. | CDR2 | SEQ. ID No. | CDR3 | SEQ. ID No. |
|---|---|---|---|---|---|---|
| 5A7 | NYGMH | 1 | VVWYDGLIKY YADSVKG | 2 | DLQPPHSPYGM DV | 3 |
| 3A2 | SYYWS | 7 | YVYNSGSTR YNPSLKS | 8 | APDDYYDSVGYY YGCPYFDS | 9 |
| 10C4 | NYAMS | 13 | AISGGGDWT YYADSVKG | 14 | DVTYLYDSSGYY YGGADRDYYFDY | 15 |

TABLE 3

Table 3: Deduced Amino Acid Sequences of CDRs in the $V_L$ of three HuMAbs.

| $V_L$ | CDR1 | SEQ. ID No. | CDR2 | SEQ. ID No. | CDR3 | SEQ. ID No. |
|---|---|---|---|---|---|---|
| 5A7 | SGSSSNI GSNDVY | 4 | NNNQRPS | 5 | AAWDDSLTVS | 6 |
| 3A2 | RASPSIA DNLA | 10 | GASTRAT | 11 | QQYSNWPRT | 12 |
| 10C4 | SGGSSNI GSNYVN | 16 | SNNQRPL | 17 | QQWDDSLNGWV | 18 |

The neutralizing activities of HuMAbs were determined as follows. The virus neutralization (VN) assay was carried out in accordance with Okuno et al. 28:1308-1313 (1990), with minor modification. MAb at a concentration of 100 mcg/ml was serially diluted four-fold with Minimum Essential Medium (MEM; Invitrogen) and incubated with 200 focus-forming units (FFU) of viruses at 37 C. for 1 hour. Then, MDCK cells were adsorbed with the mixtures at 37 C. for 1 hour. After incubation for 12 hours, the cells were fixed and subjected to IFA. The lowest concentration of MAb that inhibited 50% of viral growth was designated the $VN_{50}$ titer. In the focus formation assay, MDCK cells in a 96-well plate were adsorbed with viruses diluted serially 10-fold at 37 deg C. for 1 hour. The cells were then washed with PBS and incubated at 37 deg C. for 12 hours. The cells were fixed and subjected to IFA.

VN assays were performed with the three HuMAbs. HuMAb 5A7 had a lower $VN_{50}$ (6.25 to 25 mcg/ml) compared with 3A2 and 10C4; however, 5A7 neutralized the Yamagata and Victoria lineages isolated during 1985 to 2006. HuMAbs 3A2 and 10C4 had a $VN_{50}$ of 0.02 to 6.25 mcg/ml for Yamagata lineage, whereas they hardly neutralized any Victoria lineage except mouse-adapted B/Ibaraki/2/1985, which was neutralized slightly by 3A2 (Table 4). To clarify the mechanism of neutralization by the three HuMAbs, HI and fusion inhibition assays were also performed. In the hemagglutinin inhibition (HI) assay, viral titers were determined with a hemagglutination assay. Briefly, the viruses were serially diluted two-fold with PBS and mixed with 0.7% (v/v) human O-type red blood cells. After incubation at room temperature for 1 hour, hemagglutination units (HAUs) were estimated. Next, HI titration was performed as follows. MAb at a concentration of 100 mcg/ml was serially diluted two-fold and mixed with 8 HAU per 50 l of viral sample. After incubation at 37 C. for 1 hour, the mixtures were further incubated with 0.7% (v/v) human red blood cells for 1 hour at room temperature. The lowest concentration of MAb that completely inhibited hemagglutination was designated the HI titer.

For the fusion inhibition assay, cell-cell fusion was accomplished as described previously (Okuno et al., Journal of Virology 67:2552-2558). Briefly, monkey kidney cell line CV-1 cells were infected with B/Florida/4/2006 at an MOI of 0.3. After incubation for 24 hours, the cells were washed with MEM and then incubated for 15 min at 37 deg C. in MEM supplemented with 2.5 mcg/ml of acetylated trypsin (Sigma, St. Louis, Mo.). After washing, the cells were incubated for 30 min with diluted HuMAbs. Thereafter, the cells were treated for 2 min at 37 deg C. with MEM supplemented with 10 mM MES and 10 mM HEPES (pH 5.5). After the medium was completely removed by washing, the cells were incubated for 3 hours. Then they were fixed with absolute methanol and stained with Giemsa (Wako, Osaka, Japan).

TABLE 4

Table 4. Characterization of HuMAbs

| HuMAb | 5A7 | 3A2 | 10C4 |
|---|---|---|---|
| VN$_{50}$ (μg/ml)[1] | | | |
| Yamagata lineage | | | |
| B/Florida/4/2006 | 6.25 | 0.10 | 0.39 |
| B/Shanghai/361/2002 | 6.25 | 6.25 | 0.39 |
| R/Johannesburg/5/1999 | 6.25 | 0.10 | 0.39 |
| B/Yamanashi/166/1998 | 6.25 | 0.10 | 0.39 |
| B/Mie/1/1993 | 6.25 | 0.10 | 0.39 |
| Victoria lineage | | | |
| B/Malaysia/2506/2004 | 6.25 | >100 | >100 |
| B/Shandong/7/1997 | 25 | >100 | >100 |
| B/Victria/2/1987 | 25 | >100 | >100 |
| Mouse-adapted B/Ibaraki/2/1985 | 25 | 100 | >100 |
| HI (μg/ml)[2] | | | |
| B/Florida/4/2006 | 25 | 0.39 | 0.39 |
| Fusion inhibition (μg/ml)[3] | | | |
| B/Florida/4/2006 | 100 | 25 | 25 |

[1] The results are shown as the lowest concentrations of purified HuMAbs that inhibited 50% of viral growth in vitro.
[2] The results are shown as the lowest concentrations of purified HuMAbs that completely inhibited hemagglutination.
[3] The results are shown as the lowest concentrations of purified HuMAbs that showed cell fusion inhibition.

Accordingly, all three HuMAbs had HI activity and also inhibited cell-cell fusion (Table 4). However, 3A2 and 10C4 showed markedly higher HI titers (0.39 mcg/ml) than 5A7 (25 mcg/ml). These results indicate that all three HuMAbs should inhibit viral binding to the cell membrane.

Example 2

To determine the epitope regions of B/Florida/4/2006 recognized by the three HuMAbs, escape mutants were selected. The escape mutants were selected by the incubation of B/Florida/4/2006 with HuMAbs. Escape mutants were selected by culturing B/Florida/4/2006 in the presence of MAb as described previously (Gulati et al., Journal of Virology 76:12274-12280), with minor modification. Viruses were incubated with MAb serially diluted 10-fold (to give final concentrations of 0.0025 to 2.5 mcg/ml) at 37 C. for 1 hour. Then MDCK cells were inoculated with the mixtures and cultured in DMEM/F-12+GlutaMAX™-I supplemented with 0.4% BSA, antibiotics, and 2 mcg/ml acetylated trypsin. After culturing for 72 hours, the supernatants were collected and subjected to VN and HI assays. Those viral samples that showed a reduced VN$_{50}$ and HI titer were subjected to direct sequencing analysis of the entire HA gene.

Direct sequencing analysis was performed as follows. Viral RNA extracted with QIAamp Viral RNA Mini Kit (Qiagen, Hilden, Germany) was subjected to one step RT-PCR (Superscript™ III One-Step RT-PCR System with Platinum® Taq High Fidelity; Invitrogen) with the following HA primer set: 5'-CAGAATTCATGAAGGCAATAATTGTACTAC-3' forward (SEQ ID NO. 27) and 5'-CTCCGCGGCCGCTTATA-GACAGATGGAGCATGAAACG-3' reverse (SEQ ID NO: 28). The PCR products were purified with Qiaquick PCR Purification Kit (Qiagen). After electrophoresis, the discrete band was extracted using the Qiaquick Gel Extraction Kit (Qiagen) and sequenced.

HA plasmids were constructed as follows. The HA gene of B/Florida/4/2006 was amplified by one step RT-PCR and inserted into the pGEM-T Easy Vector (Promega, Madison, Wis.). Mutant and truncated HA genes were generated by site-directed mutagenic PCR (GeneTailor™ Site-Directed Mutagenesis System; Invitrogen) and conventional PCR (Expand High Fidelity$^{PLUS}$ PCR System; Roche), respectively, using the HA plasmid of B/Florida/4/2006 inserted into pGEM-T easy vector. Each of the plasmids was subcloned into the expression vector pCAGGS/MCSII (Ueda et al., Journal of Virology 84: 3068-3078). The expression plasmids were transfected into human embryonic kidney 293T cells with lipofectamine2000 (Invitrogen) according to the manufacturer's instructions.

The amino acid sequences of the HA protein in the escape mutants were compared with the original B/Florida/4/2006. Asterisks in FIG. 1 indicate the amino acid residues different between the original virus and the escape mutants. Interestingly, each escape mutant of 3A2 and 10C4 had amino acid substitutions at identical positions 194D and 196T; amino acid numbering was started after the signal peptide (Wang et al., Journal of Virology 82:3011-3020). These positions are located at the 190-helix antigenic site near the receptor-binding site (Wang et al., Journal of Virology 82:3011-3020). Remarkably, in the presence of serially diluted 5A7, escape mutants were not established even after the virus was passaged ten times, implying that the amino acid sequence recognized by 5A7 was essential for viral survival. HuMAb 5A7 reacted to the HA0 protein by Western blotting under reducing conditions, suggesting that 5A7 had a sequential epitope. Thus, the epitope region of 5A7 was further investigated using HA truncation vectors containing HA segments of varying length. Western blotting with 5A7 was carried out on 293T cells transfected with the truncated HA expression vectors. HuMAb 5A7 reacted with truncated HA segments that included amino acid residues 1 to 324 but not to those with residues 1 to 314 (FIG. 2). These results indicate that 5A7 recognizes amino acid residues between 315 to 324, IGNCPI-WVKT (SEQ. ID NO. 44) in the HA protein, which locates near the C terminal of the HA1 protein. Notably, this region is a highly conserved domain in influenza B viruses.

Example 3

Figure 3:
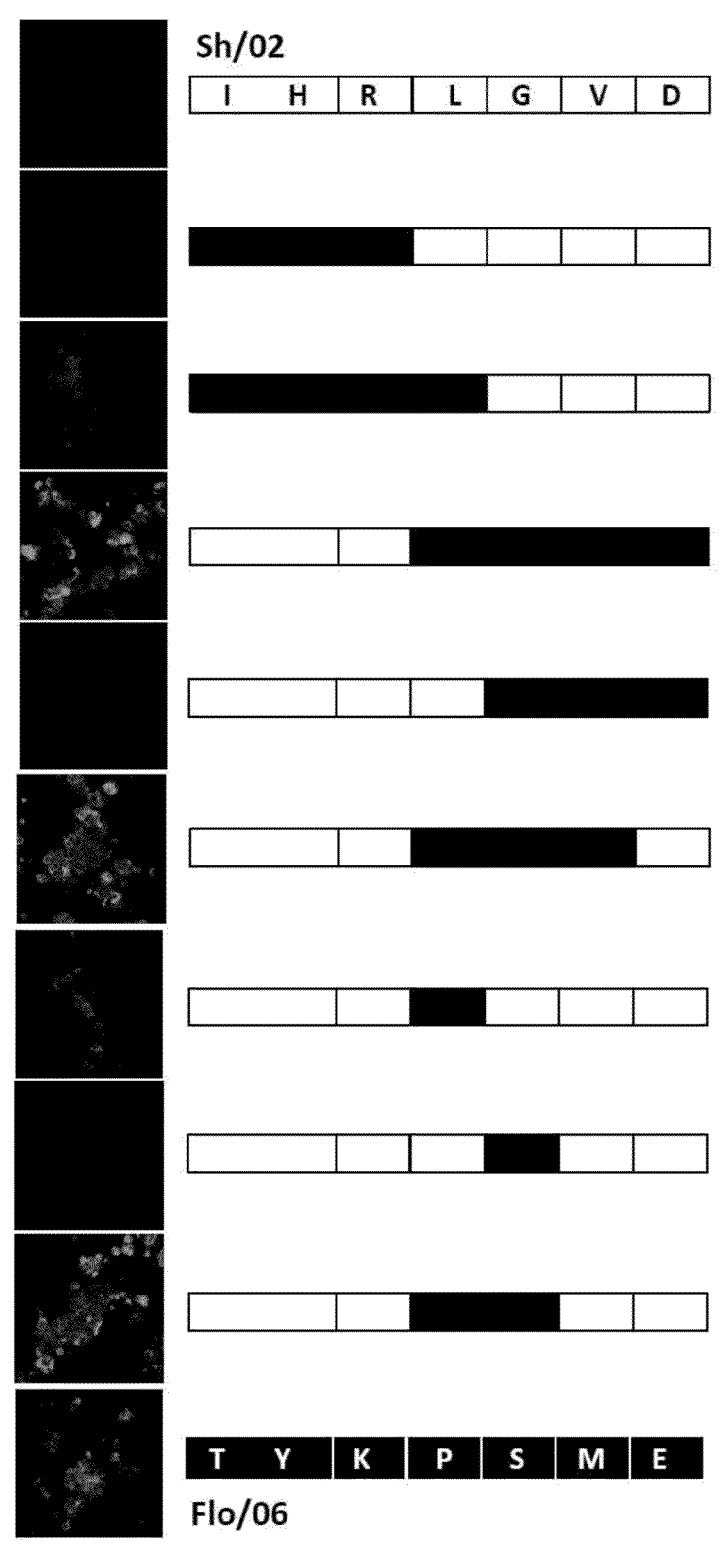
Figure 4:
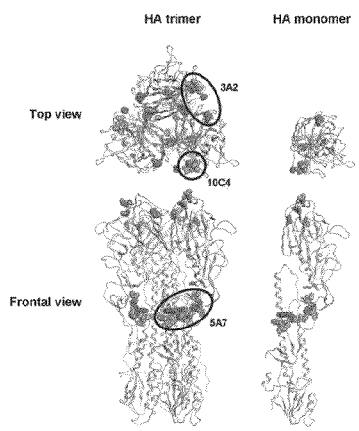
FIG. 4 shows an epitope map of the HuMAbs in three-dimensional structure of the HA protein.
Figure 5:
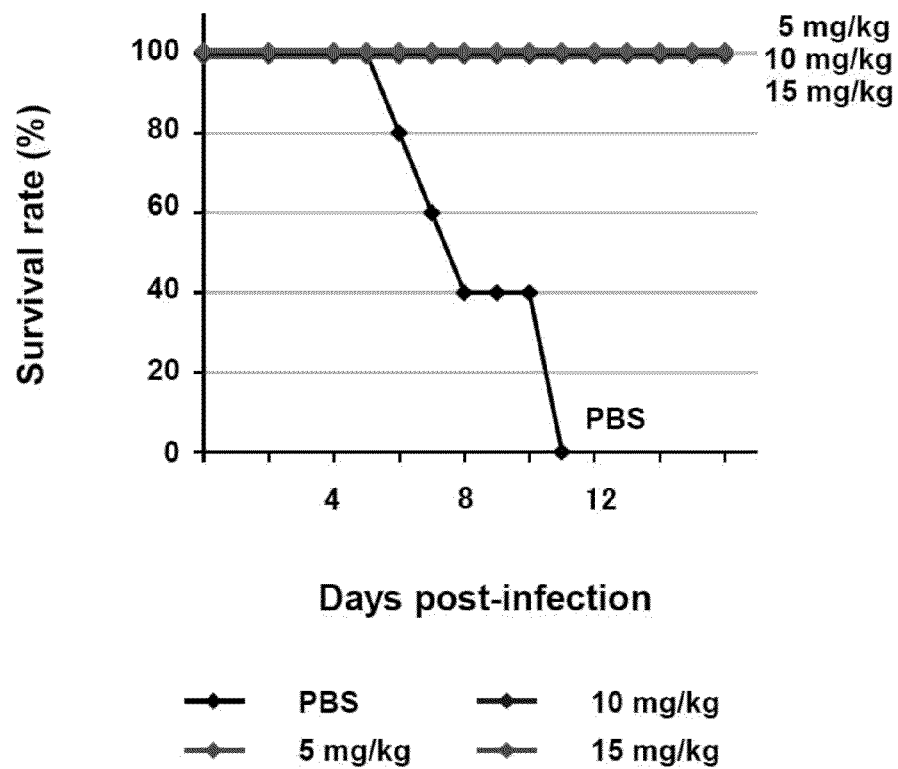
FIG. 5 shows the therapeutic efficacy of 5A7 in mice. Mice were treated intraperitoneally with HuMAb at 5, 10, or 15 mg/kg or with PBS at 4 hours post-challenge with a lethal dose ($2.5 \times 10^4$ FFU/mouse) of mouse-adapted B/Ibaraki/2/ 1985. Survival and body weight were checked daily. Each group consists of five mice. Body weight is shown as the mean+ or −SEM of five mice.
Figure 6:
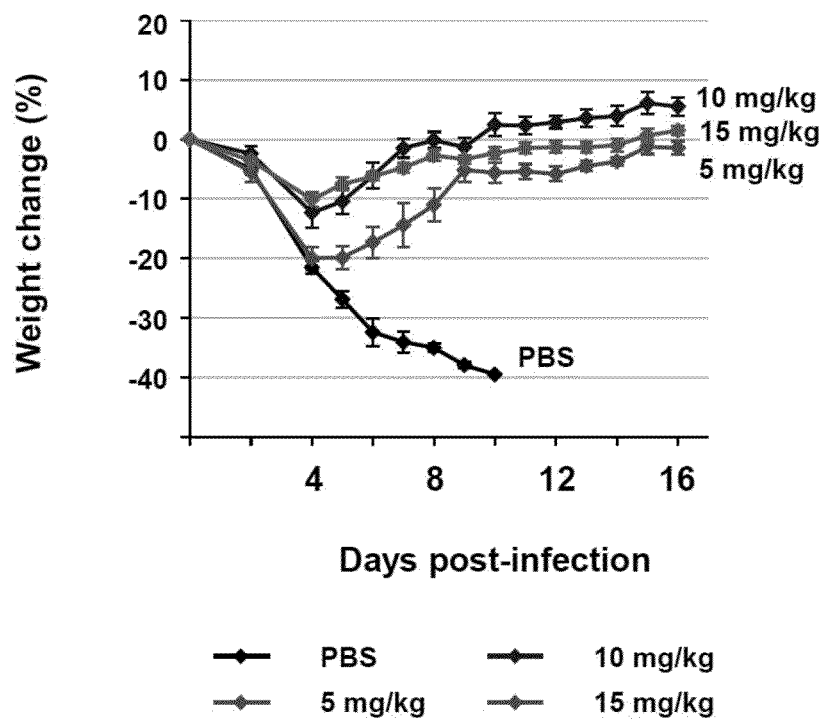
FIG. 6 shows the therapeutic efficacy of 5A7 in mice. Mice were treated intraperitoneally with HuMAb at 5, 10, or 15 mg/kg or with PBS at 4 hours post-challenge with a lethal dose ($2.5 \times 10^4$ FFU/mouse) of mouse-adapted B/Ibaraki/2/ 1985. Survival and body weight were checked daily. Each group consists of five mice. Body weight is shown as the mean+ or −SEM of five mice.
Figure 7:
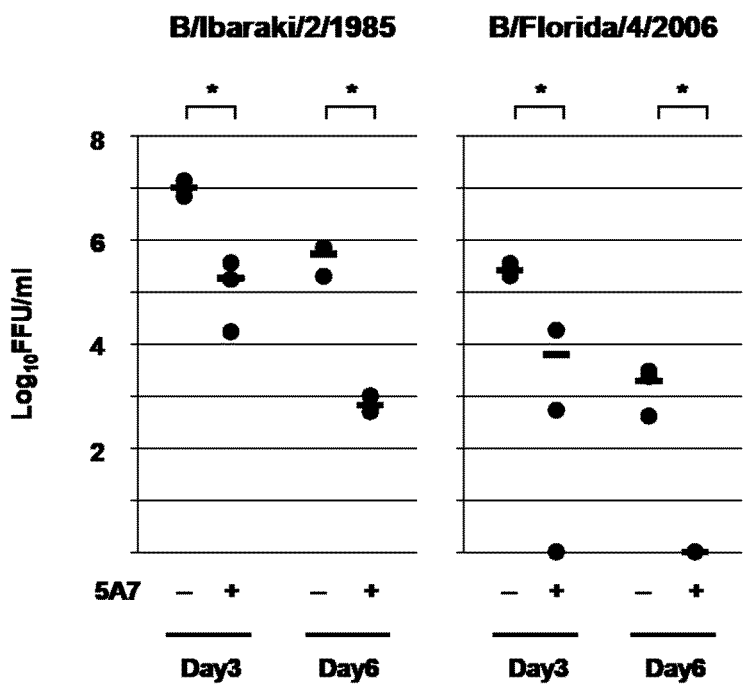
FIG. 7 shows mice treated with 5A7 at 10 mg/kg or with PBS at 4 hours post-challenge with $2.5 \times 10^4$ FFU/mouse mouse-adapted B/Ibaraki/2/1985 (left panel) and $5.0 \times 10^3$ FFU/mouse B/Florida/4/2006 (right panel). The titers in lungs were calculated at 3 and 6 days post-infection. Each group consists of three mice. Black bars are mean values. Asterisks denote P<0.05 compared to the PBS-treated group.
Figure 8:
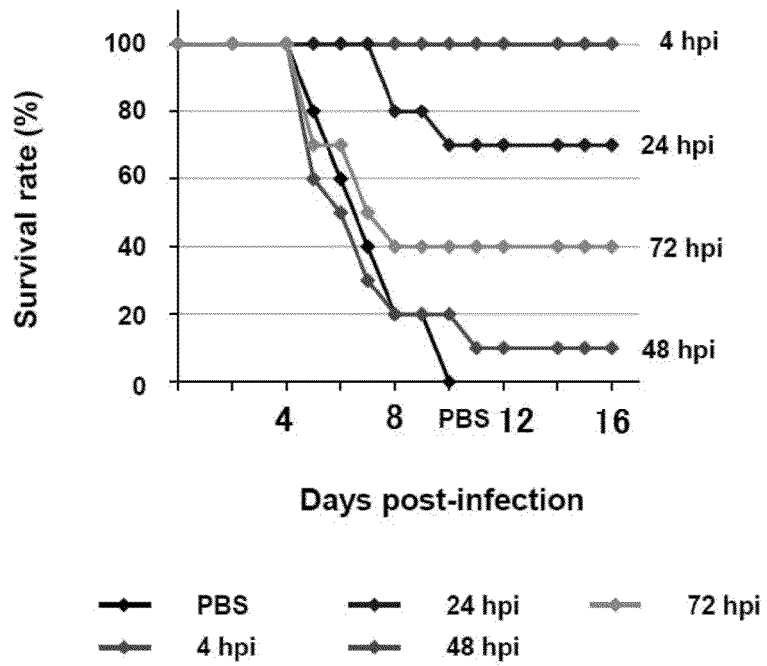
FIG. 8 shows that mice were given 10 mg/kg HuMAb or PBS at 4, 24, 48, or 72 hours post-infection (hpi) with mouse-adapted B/Ibaraki/2/1985 ($2.5 \times 10^4$ FFU/mouse). Survival and body weight were checked daily. Each group consists of ten mice. Body weight is shown as the mean+ or −SEM of ten mice.
Figure 9:
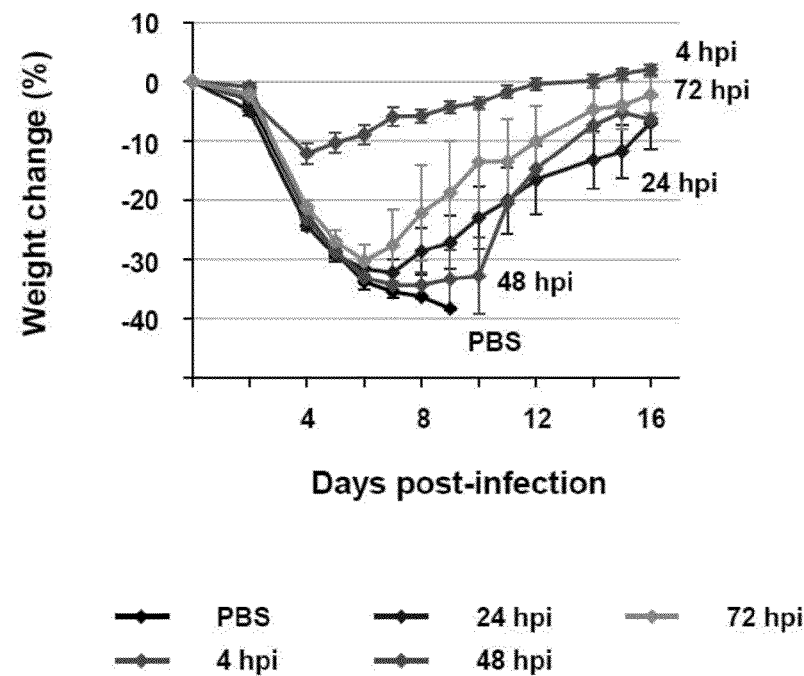
FIG. 9 shows that mice were given 10 mg/kg HuMAb or PBS at 4, 24, 48, or 72 hours post-infection (hpi) with mouse-adapted B/Ibaraki/2/1985 ($2.5 \times 10^4$ FFU/mouse). Survival and body weight were checked daily. Each group consists of ten mice. Body weight is shown as the mean+ or −SEM of ten mice.
Figure 10:
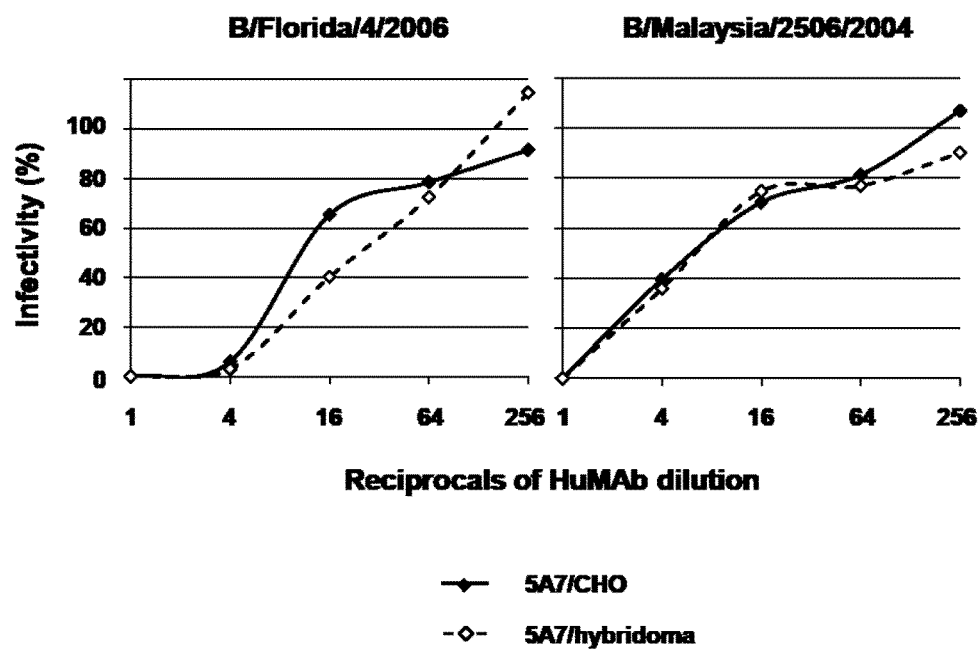
FIG. 10 shows an in vitro neutralization assay using synthesized 5A7 from CHO-K1 cells. The infectivity of B/Florida/4/2006 and B/Malaysia/2506/2004 were measured in the presence of synthesized 5A7 from CHO-K1 (5A7/

HuMAb 3A2 showed low reactivity against B/Shanghai/361/2002 and was therefore examined for an additional distinct epitope region. To do this, various chimeric sequences of HA were constructed from B/Florida/4/2006 and B/Shanghai/361/2002, which differ at seven residues (positions 37, 40, 88, 131, 227, 249, 456), expressed in plasmids, and transfected into 293T cells. IFA of the chimeric HA proteins expressed in 293T cells showed that 131P and 227S were essential for the reaction with 3A2 (FIG. 3). These results indicate that the epitope of 3A2 is dependent on residues at positions 131, 194, 196, and 227, and the epitope of 10C4 is dependent on residues at positions 194 and 196. The epitope regions to which the three HuMAbs map are shown in a HA trimer three-dimensional model in FIG. 4. HuMAbs 3A2 and 10C4 recognized the top of the globular head including the 190-helix antigenic site, whereas 5A7 reacted with the stalk region distant from the viral membrane.

HuMAb, 5A7 recognizes the stalk region of the HA protein, as do almost all broadly neutralizing MAbs for influenza A viruses. The amino acid sequence in the stalk region is highly conserved, implying that the amino acid residues would not easily mutate. Indeed, the amino acid residues in the epitope region did not mutate even when the virus was passaged ten times under 5A7-treatment conditions, whereas mutants developed quickly in the presence of 3A2 or 10C4. Failure to establish escape mutants in the presence of 5A7 is an advantage for this HuMAb as a therapeutic candidate. Although 5A7 reacted with both of Yamagata and Victoria lineages, the concentration required for $VN_{50}$ was higher than those of 3A2 and 10C4. Such results can be explained by either a difference in binding affinity or in physical accessibility of HuMAbs to the epitope region. Although binding affinity was not examined in this study, accessibility can be estimated using epitope mapping. HuMAbs 3A2 and 10C4 recognized the 190-helix site distant from the viral membrane, whereas the epitope region of 5A7 localized to the stalk region, indicating that 5A7 would have more difficulty physically accessing the HA protein. Modification of the HuMAb structure and improvement of binding affinity should lead to the development of better therapeutic antibodies.

MAbs recognizing the globular head show strong HI activity, whereas those against the stalk region usually do not show any. Thus, it is considered that MAbs against the globular head inhibit the receptor binding step and that MAbs against the stalk region inhibit the fusion step in viral replication. The HuMAbs that recognize the 190-helix in the globular head near the receptor binding site, 3A2 and 10C4, did in fact have strong HI activities, suggesting that these HuMAbs inhibited binding to the receptor. Surprisingly, 5A7 also showed weak HI activity, implying that 5A7 would also inhibit the binding step. It would be attributed that 5A7 recognizes the stalk region distal from the viral membrane, whereas MAbs that do not show HI activity recognize a more proximal position of the stalk. All three HuMAbs also showed fusion inhibition activity. HuMAbs bound to the HA protein could secondarily disturb the structural change of HA depending on low pH.

Example 4

The activity of 5A7 as a passive transfer therapy in influenza B viral infection was examined in mice. In the passive transfer experiments, before infection, mice were anesthetized by intraperitoneal administration of pentobarbital sodium (Somnopentyl; Kyoritsu Seiyaku Corporation, Tokyo, Japan). Six-week old female BALB/c mice from Japan SLC Inc. were used. Mice were given 5, 10, or 15 mg/kg HuMAb intraperitoneally at 4, 24, 48, or 72 hours after challenge with 25 mcl (microliter) mouse-adapted B/Ibaraki/2/1985 virus at a lethal dose ($2.5\times10^4$ FFU/mouse). Mice were weighed daily and sacrificed if they fell to 60% of starting weight. To titrate the viruses in the infected lungs, B/Ibaraki/2/1985 or B/Florida/4/2006 were infected at $2.5\times10^4$ or $5.0\times10^3$ FFU/mouse, respectively. The lungs were harvested 3 and 6 days post-infection and virus titers in lung homogenates were determined by focus-forming assay.

Mice were treated intraperitoneally with 5, 10, or 15 mg/kg 5A7 at 4 hours post-challenge with a lethal dose of mouse-adapted B/Ibaraki/2/1985. Survival rate and weight change were checked daily and when the body weight had dropped to less than 60% of starting weight, mice were sacrificed. Complete therapeutic efficacy against the virus was seen with each dose of 5A7 tested (FIG. 5). The weight change was particularly mild in the groups treated with 5A7 at 10 or 15 mg/kg (FIG. 6). In mice treated with 10 mg/kg 5A7, the viral load in the lungs was titrated three and six days post-infection with mouse-adapted B/Ibaraki/2/1985 or B/Florida/4/2006. The viral titers were significantly lower in 5A7-treated mice compared to untreated controls for both viral infections (FIG. 7). Finally, mice were given 5A7 at 10 mg/kg intraperitoneally at 4, 24, 48, or 72 hours post-challenge with a lethal dose of mouse-adapted B/Ibaraki/2/1985, and the survival rate and weight change were monitored. When injected four hours post-infection, 5A7 treatment showed complete therapeutic efficacy. Notably, most of the mice were alive in the 5A7-treated group at 24 hours post-infection. Moreover, several mice survived even after treatment with 5A7 more than 48 hours post-infection (FIGS. 8 and 9). These results indicate that 5A7 has the potential for development as a therapy against influenza B viral infection.

Mouse-adapted B/Ibaraki/2/1985 was used to examine the kinetics of survival rate and weight change in the passive transfer experiments as other viral strains are not lethal to mice even if passaged several times in vivo. HuMAb 5A7 protected mice against mouse-adapted B/Ibaraki/2/1985 challenge even when administered 72 hours post-infection, although 5A7 had shown the lowest sensitivity to mouse-adapted B/Ibaraki/2/1985 in vitro. These results suggested that 5A7 would have therapeutic efficacy against a wide spectrum of influenza B viruses, and in fact the lung viral titers of both mouse-adapted B/Ibaraki/2/1985 and B/Florida/4/2006 were reduced significantly under 5A7-treatment conditions.

Example 5

The neutralizing efficacy of CHO-K1-derived 5A7 was examined in vitro. 5A7 was synthesized in CHO-K1 cells and examined for neutralizing efficacy against influenza B viruses. CHO-K1 cells were transfected with full-length variable region genes of 5A7 in the pQC vector to establish a stable cell line secreting 5A7 (5A7/CHO-K1). For stable expression using mammalian cells, CHO-K1 cells were cultured in 5% $CO_2$ at 37 deg C. in DMEM containing 10% fetal bovine serum. Cells grown on 6-well plates (Corning, Corning, N.Y.) were used for transfection with pQCXIP-hCH and pQCXIH-hC lambda expression vectors using Lipofectamine2000 transfection reagent (Invitrogen). Transfected cells were incubated in 5% $CO_2$ at 37 deg C. in DMEM with 1 mcg/ml of puromycin and 100 mcg/ml of hygromycin for 3 weeks. Cells were then replated to 15-cm dishes (Corning) and incubated, and colonies were picked and cultured as putative cell lines stably expressing IgG. The transformants at 90% confluence on 15-cm dishes had the medium changed to serum-free Nutrient Mixture F-12 Ham's (Sigma), cells were then cultured in 5% $CO_2$ at 37 deg C. for 1 week. Recombinant IgGs were purified from culture medium using HiTrap Protein G HP Columns. The purified IgGs were dialyzed against PBS and then concentrated using an Amicon Ultra Centrifugal Filter (Millipore, Billerica, Mass.). In vitro viral neutralization tests were performed using purified 5A7/CHO-K1, and neutralizing activity was found against both the viral strains examined (B/Florida/4/2006 and B/Malaysia/2506/2004). Notably, the neutralizing activity of 5A7/CHO-K1 was similar to that of 5A7 produced by the hybridoma (FIG. 10).

Example 6

HuMabs 5A7, 3A2 and 10C4 were subjected to surface plasmon resonance analysis to examine their binding affinities. Each HuMab was immobilized on the surface of the sensor chip. The vaccine antigen, Ha protein of B/Florida/4/2006, at concentrations 12.5, 25, 50, 100 and 200 nM was consecutively injected on the chip surface and the association and dissociation phases were monitored. KD value could not be calculated for 5A7 precisely as it was difficult to dissociate from HA (Table 5).

TABLE 5

Kinetic constants of HuMAbs binding to influenza B virus-derived HA.

|  | kon[1] ($S^{-1}$) | koff[2] ($M^{-1}S^{-1}$) | $K_D$ (M) |
|---|---|---|---|
| 5A7 | $1.8 \times 10^3$ | $<1.0 \times 10^{-5}$ | $<5.6 \times 10^{-9}$ |
| 3A2 | $5.3 \times 10^4$ | $2.1 \times 10^{-5}$ | $4.0 \times 10^{-10}$ |
| 10C4 | $1.6 \times 10^4$ | $2.8 \times 10^{-5}$ | $1.8 \times 10^{-9}$ |

[1]Association rate constant.
[2]Dissociation rate constant.

Sequences of the $V_H$ and $V_L$ region of the three HuMAbs were compared and analyzed to the closest germline sequences using IgBlast software in NCBI database. These three HuMAbs were derived from different germ lines except D region $V_H$ of 3A2 and 10C4 (FIG. 11-13).

REFERENCES

Aoki et al., "Early Administration of Oral Oseltamivir Increases the Benefits of Influenza Treatment. The Journal of Antimicrobial Chemotherapy," 51:123-129 (2003).

Carrat et al., "Influenza Vaccine: The Challenge of Antigenic Drift," Vaccine, 25:6852-6862 (2007).

Chen et al., "Protection Against Influenza B Virus Infection by Immunization with DNA Vaccines," Vaccine, 19:1446-1455 (2001).

Corti et al., "A Neutralizing Antibody Selected from Plasma Cells that Binds to Group 1 and Group 2 Influenza A Hemagglutinins," Science, 333:850-856 (2011).

Dreyfus et al., "Highly conserved protective epitopes on influenza B viruses," Science, 337: 1343-1348 (2012)

Ekiert et al., "Antibody Recognition of a Highly Conserved Influenza Virus Epitope," Science, 324:246-251 (2009).

Ekiert et al., "A Highly Conserved Neutralizing Epitope on Group 2 Influenza A Viruses," Science, 333:843-850 (2011).

Gulati et al., "Antibody Epitopes on the Neuraminidase of a Recent H3N2 Influenza Virus," Journal of Virology, 76:12274-12280 (2002).

Hay et al., "The Evolution of Human Influenza Viruses," Philosophical Transactions of the Royal Society of London, 356:1861-1870 (2001).

Kiso et al., "Resistant Influenza A Viruses in Children Treated with Oseltamivir: Descriptive Study," Lancet, 364:759-765 (2004).

Knossow et al., "Mechanism of Neutralization of Influenza Virus Infectivity by Antibodies," Virology, 302:294-298 (2002).

Kubota-Koketsu et al., "Broad Neutralizing Human Monoclonal Antibodies Against Influenza Virus from Vaccinated Healthy Donors," Biochemical and Biophysical Research Communications, 387:180-185 (2009).

Lambert et al., "Influenza Vaccines for the Future," The New England Journal of Medicine, 363:2036-2044 (2010).

Lin et al., "Recent Changes Among Human Influenza Viruses," Virus Research, 103:47-52 (2004).

Lowen et al., "Influenza Virus Transmission: Basic Science and Implications for the Use of Antiviral Drugs During a Pandemic," Infectious Disorders Drug Targets, 7:318-328 (2007).

Marasco et al., "The Growth and Potential of Human Antiviral Monoclonal Antibody Therapeutics," Nature Biotechnology, 25:1421-1434 (2007).

Nobusawa et al., "Comparison of the Mutation Rates of Human Influenza A and B Viruses," Journal of Virology, 80:3675-3678 (2006).

Okuno et al., "A Common Neutralizing Epitope Conserved Between the Hemagglutinins of Influenza A Virus H1 and H2 Strains," Journal of Virology, 67:2552-2558 (1993).

Okuno et al., "Rapid Focus Reduction Neutralization Test of Influenza A and B Viruses in Microtiter System," Journal of Clinical Microbiology, 28:1308-1313 (1990).

Reece, "Neuraminidase Inhibitor Resistance in Influenza Viruses," Journal of Medical Virology, 79:1577-1586 (2007).

Sui et al., "Structural and Functional Bases for Broad-Spectrum Neutralization of Avian and Human Influenza A Viruses," Nature Structural & Molecular Biology, 16:265-273 (2009).

Ueda et al., "Highly Pathogenic H5N1 Avian Influenza Virus Induces Extracellular Ca2+ Influx, Leading to Apoptosis in Avian Cells," Journal of Virology, 84:3068-3078 (2010).

Wang et al., "Crystal Structure of Unliganded Influenza B Virus Hemagglutinin," Journal of Virology, 82:3011-3020 (2008).

Webster et al., "Analysis of Antigenic Drift In The Hemagglutinin Molecule Of Influenza B Virus With Monoclonal Antibodies," The Journal of General Virology, 54:243-251 (1981).

WHO, "Influenza (Seasonal)," Fact Sheet No. 211 (2009).

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

The invention claimed is:

1. An anti-human influenza virus monoclonal antibody or antigen-binding fragment thereof, comprising:
a heavy chain variable region comprising:
   a first complementarity determining region (CDR1) having an amino acid sequence comprising SEQ ID NO: 1;
   a second complementarity determining region (CDR2) having an amino acid sequence comprising SEQ ID NO: 2; and
   a third complementarity determining region (CDR3) having an amino acid sequence comprising SEQ ID NO: 3; and
a light chain variable region comprising:
   a first complementarity determining region (CDR1) having an amino acid sequence comprising SEQ ID NO: 4;
   a second complementarity determining region (CDR2) having an amino acid sequence comprising SEQ ID NO: 5; and
   a third complementarity determining region (CDR3) having an amino acid sequence comprising SEQ ID NO: 6.

2. An anti-human influenza virus monoclonal antibody or antigen-binding fragment thereof, comprising:
a heavy chain variable region comprising:
   a first complementarity determining region (CDR1) having an amino acid sequence comprising SEQ ID NO: 7;
   a second complementarity determining region (CDR2) having an amino acid sequence comprising SEQ ID NO:8; and
   a third complementarity determining region (CDR3) having an amino acid sequence comprising SEQ ID NO: 9; and
a light chain variable region comprising:
   a first complementarity determining region (CDR1) having an amino acid sequence comprising SEQ ID NO: 10;
   a second complementarity determining region (CDR2) having an amino acid sequence comprising SEQ ID NO: 11; and
   a third complementarity determining region (CDR3) having an amino acid sequence comprising SEQ ID NO: 12.

3. An anti-human influenza virus monoclonal antibody or antigen-binding fragment thereof, comprising:
a heavy chain variable region comprising:
   a first complementarity determining region (CDR1) having an amino acid sequence comprising SEQ ID NO:13;

a second complementarity determining region (CDR2) having an amino acid sequence comprising SEQ ID NO: 14; and a third complementarity determining region (CDR3) having an amino acid sequence comprising SEQ ID NO:15; and a light chain variable region comprising:

a first complementarity determining region (CDR1) having an amino acid sequence comprising SEQ ID NO: 16;

a second complementarity determining region (CDR2) having an amino acid sequence comprising SEQ ID NO: 17; and a third complementarity determining region (CDR3) having an amino acid sequence comprising SEQ ID NO: 18.

4. An anti-human influenza virus monoclonal antibody or antigen-binding fragment thereof, which has a neutralization activity against a human influenza B virus and recognizes the amino acid residues of an hemagglutinin (HA) protein at positions corresponding to any one of the following positions (i) and (ii):

(i) position 315 to 324 of SEQ ID NO: 29; and (ii) positions 131, 194, 196 and 227 of SEQ ID NO: 29.

5. A pharmaceutical composition comprising the anti-human influenza virus monoclonal antibody or antigen-binding fragment thereof of any one of claims 1 to 3 and 4, and a pharmacologically acceptable carrier.

6. A kit for at least one of the prevention, the treatment, and the detection of human influenza B in a human subject comprising the anti-human influenza virus monoclonal antibody or antigen-binding fragment thereof of any one of claims 1 to 3 and 4.

7. A method of treating or preventing human influenza B virus infection in a human subject, comprising administering to the human subject an effective amount of the anti-human influenza B virus monoclonal antibody or antigen-binding fragment thereof of any one of claims 1 to 3 and 4.

8. A method of detecting human influenza B in a human subject comprising;

contacting a sample from the human subject with the anti-human influenza B virus antibody or antigen-binding fragment thereof of any one of claims 1 to 3 and 4; and detecting the presence or absence of a human influenza B virus in the human subject based on whether the antibody binds a hemagglutinin (HA) protein of the human influenza B virus.

9. A DNA which encodes the anti-human influenza virus monoclonal antibody or antigen-binding fragment thereof of any one of claims 1 to 3 and 4.

10. A method for producing an anti-human influenza B virus human monoclonal antibody or antigen-binding fragment thereof comprising:

placing the DNA of claim 9 into an expression vector, transfecting the vector into a host cell, and synthesizing the monoclonal antibody or antigen-binding fragment thereof in the host cell.

* * * * *

SEQUENCE LISTING

```
<160> NUMBER OF SEQ ID NOS: 44

<210> SEQ ID NO 1
<211> LENGTH: 5
<212> TYPE: PRT
<213> ORGANISM: Artificial Sequence
<220> FEATURE:
```

<223> OTHER INFORMATION: Amino acid sequence of IgG (5A7 VH CDR1)

<400> SEQUENCE: 1

Asn Tyr Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Amino acid sequence of IgG (5A7 VH CDR2)

<400> SEQUENCE: 2

Val Val Trp Tyr Asp Gly Leu Ile Lys Tyr Tyr Ala Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Amino acid sequence of IgG (5A7 VH CDR3)

<400> SEQUENCE: 3

Asp Leu Gln Pro Pro His Ser Pro Tyr Gly Met Asp Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Amino acid sequence of IgG (5A7 VL CDR1)

<400> SEQUENCE: 4

Ser Gly Ser Ser Ser Asn Ile Gly Ser Asn Asp Val Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Amino acid sequence of IgG (5A7 VL CDR2)

<400> SEQUENCE: 5

Asn Asn Asn Gln Arg Pro Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Amino acid sequence of IgG (5A7 VL CDR3)

<400> SEQUENCE: 6

Ala Ala Trp Asp Asp Ser Leu Thr Val Ser
1               5                   10

<210> SEQ ID NO 7
<211> LENGTH: 5
<212> TYPE: PRT
<213> ORGANISM: Artificial Sequence

```
<220> FEATURE:
<223> OTHER INFORMATION: Amino acid sequence of IgG (3A2 VH CDR1)

<400> SEQUENCE: 7

Ser Tyr Tyr Trp Ser
1               5

<210> SEQ ID NO 8
<211> LENGTH: 16
<212> TYPE: PRT
<213> ORGANISM: Artificial Sequence
<220> FEATURE:
<223> OTHER INFORMATION: Amino acid sequence of IgG (3A2 VH CDR2)

<400> SEQUENCE: 8

Tyr Val Tyr Asn Ser Gly Ser Thr Arg Tyr Asn Pro Ser Leu Lys Ser
1               5                   10                  15

<210> SEQ ID NO 9
<211> LENGTH: 20
<212> TYPE: PRT
<213> ORGANISM: Artificial Sequence
<220> FEATURE:
<223> OTHER INFORMATION: Amino acid sequence of IgG (3A2 VH CDR3)

<400> SEQUENCE: 9

Ala Pro Asp Asp Tyr Tyr Asp Ser Val Gly Tyr Tyr Tyr Gly Cys Pro
1               5                   10                  15

Tyr Phe Asp Ser
            20

<210> SEQ ID NO 10
<211> LENGTH: 11
<212> TYPE: PRT
<213> ORGANISM: Artificial Sequence
<220> FEATURE:
<223> OTHER INFORMATION: Amino acid sequence of IgG (3A2 VL CDR1)

<400> SEQUENCE: 10

Arg Ala Ser Pro Ser Ile Ala Asp Asn Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Amino acid sequence of IgG (3A2 VL CDR2)

<400> SEQUENCE: 11

Gly Ala Ser Thr Arg Ala Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Amino acid sequence of IgG (3A2 VL CDR3)

<400> SEQUENCE: 12

Gln Gln Tyr Ser Asn Trp Pro Arg Thr
1               5

<210> SEQ ID NO 13
<211> LENGTH: 5
```

```
<212> TYPE: PRT
<213> ORGANISM: Artificial Sequence
<220> FEATURE:
<223> OTHER INFORMATION: Amino acid sequence of IgG (10C4 VH CDR1)

<400> SEQUENCE: 13

Asn Tyr Ala Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Amino acid sequence of IgG (10C4 VH CDR2)

<400> SEQUENCE: 14

Ala Ile Ser Gly Gly Gly Asp Trp Thr Tyr Tyr Ala Asp Ser Val Lys
1               5                   10                  15

Gly

<210> SEQ ID NO 15
<211> LENGTH: 24
<212> TYPE: PRT
<213> ORGANISM: Artificial Sequence
<220> FEATURE:
<223> OTHER INFORMATION: Amino acid sequence of IgG (10C4 VH CDR3)

<400> SEQUENCE: 15

Asp Val Thr Tyr Leu Tyr Asp Ser Ser Gly Tyr Tyr Tyr Gly Gly Ala
1               5                   10                  15

Asp Arg Asp Tyr Tyr Phe Asp Tyr
            20

<210> SEQ ID NO 16
<211> LENGTH: 13
<212> TYPE: PRT
<213> ORGANISM: Artificial Sequence
<220> FEATURE:
<223> OTHER INFORMATION: Amino acid sequence of IgG (10C4 VL CDR1)

<400> SEQUENCE: 16

Ser Gly Gly Ser Ser Asn Ile Gly Ser Asn Tyr Val Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Amino acid sequence of IgG (10C4 VL CDR2)

<400> SEQUENCE: 17

Ser Asn Asn Gln Arg Pro Leu
1               5

<210> SEQ ID NO 18
<211> LENGTH: 11
<212> TYPE: PRT
<213> ORGANISM: Artificial Sequence
<220> FEATURE:
<223> OTHER INFORMATION: Amino acid sequence of IgG (10C4 VL CDR3)

<400> SEQUENCE: 18

Gln Gln Trp Asp Asp Ser Leu Asn Gly Trp Val
1               5                   10
```

<210> SEQ ID NO 19
<211> LENGTH: 24
<212> TYPE: DNA
<213> ORGANISM: Artificial Sequence
<220> FEATURE:
<223> OTHER INFORMATION: Primer sequence of H-chain-forward

<400> SEQUENCE: 19
atggagtttg ggctgagctg ggtt                                    24

<210> SEQ ID NO 20
<211> LENGTH: 25
<212> TYPE: DNA
<213> ORGANISM: Artificial Sequence
<220> FEATURE:
<223> OTHER INFORMATION: Primer sequence of H-chain-reverse

<400> SEQUENCE: 20
ctcccgcggc tttgtcttgg catta                                   25

<210> SEQ ID NO 21
<211> LENGTH: 24
<212> TYPE: DNA
<213> ORGANISM: Artificial Sequence
<220> FEATURE:
<223> OTHER INFORMATION: Primer sequence of L-chain-forward

<400> SEQUENCE: 21
atggcctggr ycycmytcyw cctm                                    24

<210> SEQ ID NO 22
<211> LENGTH: 25
<212> TYPE: DNA
<213> ORGANISM: Artificial Sequence
<220> FEATURE:
<223> OTHER INFORMATION: Primer sequence of L-chain-reverse

<400> SEQUENCE: 22
tggcagctgt agcttctgtg ggact                                   25

<210> SEQ ID NO 23
<211> LENGTH: 30
<212> TYPE: DNA
<213> ORGANISM: Artificial Sequence
<220> FEATURE:
<223> OTHER INFORMATION: Primer sequence of HC_5Fw_NotI; H-chain-forward

<400> SEQUENCE: 23
atttgcggcc gccatggagt ttgggctgag                              30

<210> SEQ ID NO 24
<211> LENGTH: 31
<212> TYPE: DNA
<213> ORGANISM: Artificial Sequence
<220> FEATURE:
<223> OTHER INFORMATION: Primer sequence of HC_Reverse_XhoI;
      H-chain-reverse

<400> SEQUENCE: 24
atactcgagg gtgccagggg gaagaccgat g                            31

<210> SEQ ID NO 25
<211> LENGTH: 30
<212> TYPE: DNA
<213> ORGANISM: Artificial Sequence -continued
<220> FEATURE:
<223> OTHER INFORMATION: Primer sequence of 5A7Lambda_18Fw_NotI; L-chain-forward

<400> SEQUENCE: 25
atttgcggcc gccatggcct gggctctgct 30

<210> SEQ ID NO 26
<211> LENGTH: 31
<212> TYPE: DNA
<213> ORGANISM: Artificial Sequence
<220> FEATURE:
<223> OTHER INFORMATION: Primer sequence of Lambda_Reverse_XhoI; L-chain-reverse

<400> SEQUENCE: 26
atactcgagg gcgggaacag agtgaccgtg g 31

<210> SEQ ID NO 27
<211> LENGTH: 30
<212> TYPE: DNA
<213> ORGANISM: Artificial Sequence
<220> FEATURE:
<223> OTHER INFORMATION: Primer sequence of HA primer forward

<400> SEQUENCE: 27
cagaattcat gaaggcaata attgtactac 30

<210> SEQ ID NO 28
<211> LENGTH: 37
<212> TYPE: DNA
<213> ORGANISM: Artificial Sequence
<220> FEATURE:
<223> OTHER INFORMATION: Primer sequence of HA primer reverse

<400> SEQUENCE: 28
ctccgcggcc gcttatagac agatggagca tgaaacg 37

<210> SEQ ID NO 29
<211> LENGTH: 569
<212> TYPE: PRT
<213> ORGANISM: Influenza B virus

<400> SEQUENCE: 29
```

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
    130                 135                 140
```

```
Asn Ala Thr Ser Lys Ser Gly Phe Phe Ala Thr Met Ala Trp Ala Val
145                 150                 155                 160

Pro Lys Asp Asn Asn Lys Asn Ala Thr Asn Pro Leu Thr Val Glu Val
                165                 170                 175

Pro Tyr Ile Cys Thr Glu Gly Glu Asp Gln Ile Thr Val Trp Gly Phe
            180                 185                 190

His Ser Asp Asp Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220

Ser Gln Ile Gly Ser Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
    290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg Gly Phe Phe Gly Ala Ile
            340                 345                 350

Ala Gly Phe Leu Glu Gly Gly Trp Glu Gly Met Ile Ala Gly Trp His
        355                 360                 365

Gly Tyr Thr Ser His Gly Ala His Gly Val Ala Val Ala Ala Asp Leu
    370                 375                 380

Lys Ser Thr Gln Glu Ala Ile Asn Lys Ile Thr Lys Asn Leu Asn Ser
385                 390                 395                 400

Leu Ser Glu Leu Glu Val Lys Asn Leu Gln Arg Leu Ser Gly Ala Met
                405                 410                 415

Asp Glu Leu His Asn Glu Ile Leu Glu Leu Asp Glu Lys Val Asp Asp
            420                 425                 430

Leu Arg Ala Asp Thr Ile Ser Ser Gln Ile Glu Leu Ala Val Leu Leu
        435                 440                 445

Ser Asn Glu Gly Ile Ile Asn Ser Glu Asp Glu His Leu Leu Ala Leu
    450                 455                 460

Glu Arg Lys Leu Lys Lys Met Leu Gly Pro Ser Ala Val Glu Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
            500                 505                 510

Phe Asp Ser Leu Asn Ile Thr Ala Ala Ser Leu Asn Asp Asp Gly Leu
        515                 520                 525

Asp Asn His Thr Ile Leu Leu Tyr Tyr Ser Thr Ala Ala Ser Ser Leu
    530                 535                 540

Ala Val Thr Leu Met Leu Ala Ile Phe Ile Val Tyr Met Val Ser Arg
545                 550                 555                 560
```

```
Asp Asn Val Ser Cys Ser Ile Cys Leu
                565

<210> SEQ ID NO 30
<211> LENGTH: 552
<212> TYPE: PRT
<213> ORGANISM: Influenza B virus

<400> SEQUENCE: 30

Arg Ile Cys Thr Gly Ile Thr Ser Ser Asn Ser Pro His Val Val Lys
1               5                   10                  15

Thr Ala Thr Gln Gly Glu Val Asn Val Thr Gly Val Ile Pro Leu Thr
                20                  25                  30

Thr Thr Pro Thr Lys Ser Tyr Phe Ala Asn Leu Lys Gly Thr Arg Thr
            35                  40                  45

Arg Gly Lys Leu Cys Pro Asp Cys Leu Asn Cys Thr Asp Leu Asp Val
        50                  55                  60

Ala Leu Gly Arg Pro Met Cys Val Gly Thr Thr Pro Ser Ala Lys Ala
65                  70                  75                  80

Ser Ile Leu His Glu Val Lys Pro Val Thr Ser Gly Cys Phe Pro Ile
                85                  90                  95

Met His Asp Arg Thr Lys Ile Arg Gln Leu Pro Asn Leu Leu Arg Gly
                100                 105                 110

Tyr Glu Asn Ile Arg Leu Ser Thr Gln Asn Val Ile Asp Ala Glu Lys
            115                 120                 125

Ala Pro Gly Gly Pro Tyr Arg Leu Gly Thr Ser Gly Ser Cys Pro Asn
        130                 135                 140

Ala Thr Ser Lys Ser Gly Phe Phe Ala Thr Met Ala Trp Ala Val Pro
145                 150                 155                 160

Lys Asp Asn Asn Lys Asn Ala Thr Asn Pro Leu Thr Val Glu Val Pro
                165                 170                 175

Tyr Ile Cys Thr Glu Gly Glu Asp Gln Ile Thr Val Trp Gly Phe His
                180                 185                 190

Ser Asp Asn Lys Ile Gln Met Lys Asn Leu Tyr Gly Asp Ser Asn Pro
            195                 200                 205

Gln Lys Phe Thr Ser Ser Ala Asn Gly Val Thr Thr His Tyr Val Ser
        210                 215                 220

Gln Ile Gly Ser Phe Pro Asp Gln Thr Glu Asp Gly Gly Leu Pro Gln
225                 230                 235                 240

Ser Gly Arg Ile Val Val Asp Tyr Met Met Gln Lys Pro Gly Lys Thr
                245                 250                 255

Gly Thr Ile Val Tyr Gln Arg Gly Val Leu Leu Pro Gln Lys Val Trp
                260                 265                 270

Cys Ala Ser Gly Arg Ser Lys Val Ile Lys Gly Ser Leu Pro Leu Ile
            275                 280                 285

Gly Glu Ala Asp Cys Leu His Glu Lys Tyr Gly Gly Leu Asn Lys Ser
        290                 295                 300

Lys Pro Tyr Tyr Thr Gly Glu His Ala Lys Ala Ile Gly Asn Cys Pro
305                 310                 315                 320

Ile Trp Val Lys Thr Pro Leu Lys Leu Ala Asn Gly Thr Lys Tyr Arg
                325                 330                 335

Pro Pro Ala Lys Leu Leu Lys Glu Arg Gly Phe Phe Gly Ala Ile Ala
                340                 345                 350

Gly Phe Leu Glu Gly Gly Trp Glu Gly Met Ile Ala Gly Trp His Gly
            355                 360                 365
```

```
Tyr Thr Ser His Gly Ala His Gly Val Ala Val Ala Ala Asp Leu Lys
            370                 375                 380

Ser Thr Gln Glu Ala Ile Asn Lys Ile Thr Lys Asn Leu Asn Ser Leu
385                 390                 395                 400

Ser Glu Leu Glu Val Lys Asn Leu Gln Arg Leu Ser Gly Ala Met Asp
                405                 410                 415

Glu Leu His Asn Glu Ile Leu Glu Leu Asp Glu Lys Val Asp Asp Leu
            420                 425                 430

Arg Ala Asp Thr Ile Ser Ser Gln Ile Glu Leu Ala Val Leu Leu Ser
        435                 440                 445

Asn Glu Gly Ile Ile Asn Ser Glu Asp Glu His Leu Leu Ala Leu Glu
450                 455                 460

Arg Lys Leu Lys Lys Met Leu Gly Pro Ser Ala Val Glu Ile Gly Asn
465                 470                 475                 480

Gly Cys Phe Glu Thr Lys His Lys Cys Asn Gln Thr Cys Leu Asp Arg
                485                 490                 495

Ile Ala Ala Gly Thr Phe Asn Ala Gly Glu Phe Ser Leu Pro Thr Phe
            500                 505                 510

Asp Ser Leu Asn Ile Thr Ala Ala Ser Leu Asn Asp Asp Gly Leu Asp
        515                 520                 525

Asn His Thr Ile Leu Leu Tyr Tyr Ser Thr Ala Ala Ser Ser Leu Ala
530                 535                 540

Val Thr Leu Met Leu Ala Ile Phe
545                 550

<210> SEQ ID NO 31
<211> LENGTH: 552
<212> TYPE: PRT
<213> ORGANISM: Influenza B virus

<400> SEQUENCE: 31

Arg Ile Cys Thr Gly Ile Thr Ser Ser Asn Ser Pro His Val Val Lys
1               5                   10                  15

Thr Ala Thr Gln Gly Glu Val Asn Val Thr Gly Val Ile Pro Leu Thr
                20                  25                  30

Thr Thr Pro Thr Lys Ser Tyr Phe Ala Asn Leu Lys Gly Thr Arg Thr
            35                  40                  45

Arg Gly Lys Leu Cys Pro Asp Cys Leu Asn Cys Thr Asp Leu Asp Val
        50                  55                  60

Ala Leu Gly Arg Pro Met Cys Val Gly Thr Thr Pro Ser Ala Lys Ala
65                  70                  75                  80

Ser Ile Leu His Glu Val Lys Pro Val Thr Ser Gly Cys Phe Pro Ile
                85                  90                  95

Met His Asp Arg Thr Lys Ile Arg Gln Leu Pro Asn Leu Leu Arg Gly
            100                 105                 110

Tyr Glu Asn Ile Arg Leu Ser Thr Gln Asn Val Ile Asp Ala Glu Lys
        115                 120                 125

Ala Pro Gly Gly Pro Tyr Arg Leu Gly Thr Ser Gly Ser Cys Pro Asn
130                 135                 140

Ala Thr Ser Lys Ser Gly Phe Phe Ala Thr Met Ala Trp Ala Val Pro
145                 150                 155                 160

Lys Asp Asn Asn Lys Asn Ala Thr Asn Pro Leu Thr Val Glu Val Pro
                165                 170                 175

Tyr Ile Cys Thr Glu Gly Glu Asp Gln Ile Thr Val Trp Gly Phe His
```

```
            180                 185                 190
Ser Asp Asn Lys Asn Gln Met Lys Asn Leu Tyr Gly Asp Ser Asn Pro
        195                 200                 205

Gln Lys Phe Thr Ser Ser Ala Asn Gly Val Thr Thr His Tyr Val Ser
    210                 215                 220

Gln Ile Gly Ser Phe Pro Asp Gln Thr Glu Asp Gly Gly Leu Pro Gln
225                 230                 235                 240

Ser Gly Arg Ile Val Val Asp Tyr Met Met Gln Lys Pro Gly Lys Thr
                245                 250                 255

Gly Thr Ile Val Tyr Gln Arg Gly Val Leu Leu Pro Gln Lys Val Trp
            260                 265                 270

Cys Ala Ser Gly Arg Ser Lys Val Ile Lys Gly Ser Leu Pro Leu Ile
        275                 280                 285

Gly Glu Ala Asp Cys Leu His Glu Lys Tyr Gly Leu Asn Lys Ser
    290                 295                 300

Lys Pro Tyr Tyr Thr Gly Glu His Ala Lys Ala Ile Gly Asn Cys Pro
305                 310                 315                 320

Ile Trp Val Lys Thr Pro Leu Lys Leu Ala Asn Gly Thr Lys Tyr Arg
                325                 330                 335

Pro Pro Ala Lys Leu Leu Lys Glu Arg Gly Phe Phe Gly Ala Ile Ala
            340                 345                 350

Gly Phe Leu Glu Gly Gly Trp Glu Gly Met Ile Ala Gly Trp His Gly
        355                 360                 365

Tyr Thr Ser His Gly Ala His Gly Val Ala Val Ala Ala Asp Leu Lys
    370                 375                 380

Ser Thr Gln Glu Ala Ile Asn Lys Ile Thr Lys Asn Leu Asn Ser Leu
385                 390                 395                 400

Ser Glu Leu Glu Val Lys Asn Leu Gln Arg Leu Ser Gly Ala Met Asp
                405                 410                 415

Glu Leu His Asn Glu Ile Leu Glu Leu Asp Glu Lys Val Asp Asp Leu
            420                 425                 430

Arg Ala Asp Thr Ile Ser Ser Gln Ile Glu Leu Ala Val Leu Leu Ser
        435                 440                 445

Asn Glu Gly Ile Ile Asn Ser Glu Asp Glu His Leu Leu Ala Leu Glu
    450                 455                 460

Arg Lys Leu Lys Lys Met Leu Gly Pro Ser Ala Val Glu Ile Gly Asn
465                 470                 475                 480

Gly Cys Phe Glu Thr Lys His Lys Cys Asn Gln Thr Cys Leu Asp Arg
                485                 490                 495

Ile Ala Ala Gly Thr Phe Asn Ala Gly Glu Phe Ser Leu Pro Thr Phe
            500                 505                 510

Asp Ser Leu Asn Ile Thr Ala Ala Ser Leu Asn Asp Asp Gly Leu Asp
        515                 520                 525

Asn His Thr Ile Leu Leu Tyr Tyr Ser Thr Ala Ala Ser Ser Leu Ala
    530                 535                 540

Val Thr Leu Met Leu Ala Ile Phe
545                 550

<210> SEQ ID NO 32
<211> LENGTH: 441
<212> TYPE: DNA
<213> ORGANISM: Artificial
<220> FEATURE:
<221> NAME/KEY: CDS
<222> LOCATION: (1)..(441)
```

<223> OTHER INFORMATION: The variable region of the heavy chain (5A7)

<400> SEQUENCE: 32

```
atg aaa cac ctg tgg ttc ttc ctc ctc ctg gtg gca gct ccc aga tgg     48
Met Lys His Leu Trp Phe Phe Leu Leu Leu Val Ala Ala Pro Arg Trp
1               5                   10                  15 gtc ctg tcc cag gtg cag ctg gtg gag tcg ggc cca gga ctg gtg aag     96
Val Leu Ser Gln Val Gln Leu Val Glu Ser Gly Pro Gly Leu Val Lys
            20                  25                  30 cct tct gag acc ctg tcc ctc acc tgc act gtc tct agt ggc tcc atc    144
Pro Ser Glu Thr Leu Ser Leu Thr Cys Thr Val Ser Ser Gly Ser Ile
        35                  40                  45 agt agt tac tac tgg agc tgg atc cgg cag ccc ccc ggg aag gga ctg    192
Ser Ser Tyr Tyr Trp Ser Trp Ile Arg Gln Pro Pro Gly Lys Gly Leu
    50                  55                  60 gag tgg att ggg tat gtc tat aac agt ggg agt acc agg tac aac ccc    240
Glu Trp Ile Gly Tyr Val Tyr Asn Ser Gly Ser Thr Arg Tyr Asn Pro
65                  70                  75                  80 tcc ctc aag agt cgc ctc acc atg tca gtg gac gcg tcc agg aag cag    288
Ser Leu Lys Ser Arg Leu Thr Met Ser Val Asp Ala Ser Arg Lys Gln
                85                  90                  95 gtc tcc ctg aag ttg agc tct gtg agt gct gcg gac acg gcc gtg tat    336
Val Ser Leu Lys Leu Ser Ser Val Ser Ala Ala Asp Thr Ala Val Tyr
            100                 105                 110 tac tgt gcg aga gcc ccg gac gat tac tat gat agt gtt ggt tat tac    384
Tyr Cys Ala Arg Ala Pro Asp Asp Tyr Tyr Asp Ser Val Gly Tyr Tyr
        115                 120                 125 tac gga tgt ccg tac ttc gac tcc tgg ggc cag gga acc ctg gtc acc    432
Tyr Gly Cys Pro Tyr Phe Asp Ser Trp Gly Gln Gly Thr Leu Val Thr
    130                 135                 140 gtc tcc tca                                                        441
Val Ser Ser
145
```

<210> SEQ ID NO 33
<211> LENGTH: 147
<212> TYPE: PRT
<213> ORGANISM: Artificial
<220> FEATURE:
<223> OTHER INFORMATION: The variable region of the heavy chain (5A7)

<400> SEQUENCE: 33

```
Met Lys His Leu Trp Phe Phe Leu Leu Leu Val Ala Ala Pro Arg Trp
1               5                   10                  15

Val Leu Ser Gln Val Gln Leu Val Glu Ser Gly Pro Gly Leu Val Lys
            20                  25                  30

Pro Ser Glu Thr Leu Ser Leu Thr Cys Thr Val Ser Ser Gly Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Val Tyr Asn Ser Gly Ser Thr Arg Tyr Asn Pro
65                  70                  75                  80

Ser Leu Lys Ser Arg Leu Thr Met Ser Val Asp Ala Ser Arg Lys Gln
                85                  90                  95

Val Ser Leu Lys Leu Ser Ser Val Ser Ala Ala Asp Thr Ala Val Tyr
            100                 105                 110

Tyr Cys Ala Arg Ala Pro Asp Asp Tyr Tyr Asp Ser Val Gly Tyr Tyr
        115                 120                 125

Tyr Gly Cys Pro Tyr Phe Asp Ser Trp Gly Gln Gly Thr Leu Val Thr
```

```
                130                 135                 140
Val Ser Ser
145

<210> SEQ ID NO 34
<211> LENGTH: 381
<212> TYPE: DNA
<213> ORGANISM: Artificial
<220> FEATURE:
<221> NAME/KEY: CDS
<222> LOCATION: (1)..(381)
<223> OTHER INFORMATION: The variable region of the lamda chain (5A7)

<400> SEQUENCE: 34 atg gaa gcc cca gcg cag ctt ctc ttc ctc ctg cta ctc tgg ctc cca      48
Met Glu Ala Pro Ala Gln Leu Leu Phe Leu Leu Leu Leu Trp Leu Pro
1               5                   10                  15 gat acc agt gga gaa ata ggg atg acg cag tct cca gcc acc ctg tct      96
Asp Thr Ser Gly Glu Ile Gly Met Thr Gln Ser Pro Ala Thr Leu Ser
            20                  25                  30 gtg tct cca ggg gaa aga gcc acc ctc ttt tgc agg gcc agt ccg agt     144
Val Ser Pro Gly Glu Arg Ala Thr Leu Phe Cys Arg Ala Ser Pro Ser
        35                  40                  45 att agc gac aac tta gcc tgg tac cag cag aaa cct ggc cag gct ccc     192
Ile Ser Asp Asn Leu Ala Trp Tyr Gln Gln Lys Pro Gly Gln Ala Pro
    50                  55                  60 agg ctc ctc ttc tat ggt gca tcc acc agg gcc act ggt atc cca gcc     240
Arg Leu Leu Phe Tyr Gly Ala Ser Thr Arg Ala Thr Gly Ile Pro Ala
65                  70                  75                  80 agg ttc agc ggc agt ggg tct ggg aca gag ttc act ctc acc atc agc     288
Arg Phe Ser Gly Ser Gly Ser Gly Thr Glu Phe Thr Leu Thr Ile Ser
                85                  90                  95 agt gtg cag tct gaa gat att gga gtt tat tat tgt cag cag tat agt     336
Ser Val Gln Ser Glu Asp Ile Gly Val Tyr Tyr Cys Gln Gln Tyr Ser
            100                 105                 110 aac tgg cct cgt act ttt ggc cag ggg acc aag ctg cag atc aaa         381
Asn Trp Pro Arg Thr Phe Gly Gln Gly Thr Lys Leu Gln Ile Lys
        115                 120                 125

<210> SEQ ID NO 35
<211> LENGTH: 127
<212> TYPE: PRT
<213> ORGANISM: Artificial
<220> FEATURE:
<223> OTHER INFORMATION: The variable region of the lamda chain (5A7)

<400> SEQUENCE: 35

Met Glu Ala Pro Ala Gln Leu Leu Phe Leu Leu Leu Leu Trp Leu Pro
1               5                   10                  15

Asp Thr Ser Gly Glu Ile Gly Met Thr Gln Ser Pro Ala Thr Leu Ser
            20                  25                  30

Val Ser Pro Gly Glu Arg Ala Thr Leu Phe Cys Arg Ala Ser Pro Ser
        35                  40                  45

Ile Ser Asp Asn Leu Ala Trp Tyr Gln Gln Lys Pro Gly Gln Ala Pro
    50                  55                  60

Arg Leu Leu Phe Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Val Gln Ser Glu Asp Ile Gly Val Tyr Tyr Cys Gln Gln Tyr Ser
            100                 105                 110
```

Asn Trp Pro Arg Thr Phe Gly Gln Gly Thr Lys Leu Gln Ile Lys
        115                 120                 125

<210> SEQ ID NO 36
<211> LENGTH: 423
<212> TYPE: DNA
<213> ORGANISM: Artificial
<220> FEATURE:
<221> NAME/KEY: CDS
<222> LOCATION: (1)..(423)
<223> OTHER INFORMATION: The variable region of the heavy chain (3A2)

<400> SEQUENCE: 36

```
atg gag ttt ggg ctg agc tgg gtt ctc ctc gtt gct ctt tta aga ggt      48
Met Glu Phe Gly Leu Ser Trp Val Leu Leu Val Ala Leu Leu Arg Gly
1               5                   10                  15 gtc cag tgt cag gtg cag ctg gtg gag tct ggg gga gac gtg gtc caa      96
Val Gln Cys Gln Val Gln Leu Val Glu Ser Gly Gly Asp Val Val Gln
            20                  25                  30 cct ggg agg tcc ctg aga ctc tcc tgc gca gcg tct gga ttc acc ttc     144
Pro Gly Arg Ser Leu Arg Leu Ser Cys Ala Ala Ser Gly Phe Thr Phe
        35                  40                  45 aat aac tat ggc atg cac tgg gtc cgc cag gct cca ggc aag ggg ctg     192
Asn Asn Tyr Gly Met His Trp Val Arg Gln Ala Pro Gly Lys Gly Leu
    50                  55                  60 gag tgg gtg gca gtt gtc tgg tat gat gga ctt att aaa tac tat gcg     240
Glu Trp Val Ala Val Val Trp Tyr Asp Gly Leu Ile Lys Tyr Tyr Ala
65                  70                  75                  80 gac tcc gtg aag ggc cga ttc acc atc tcc aga gac aat tcg aaa aac     288
Asp Ser Val Lys Gly Arg Phe Thr Ile Ser Arg Asp Asn Ser Lys Asn
                85                  90                  95 acc ctg tat ctg caa atg aac acc ctg aga gcc gag gac atg ggt gtc     336
Thr Leu Tyr Leu Gln Met Asn Thr Leu Arg Ala Glu Asp Met Gly Val
            100                 105                 110 tat tac tgt gcg aga gat cta cag cct ccc cat tca ccc tac ggt atg     384
Tyr Tyr Cys Ala Arg Asp Leu Gln Pro Pro His Ser Pro Tyr Gly Met
        115                 120                 125 gac gtc tgg ggc caa ggg acc acg gtc acc gtc tcc tca                 423
Asp Val Trp Gly Gln Gly Thr Thr Val Thr Val Ser Ser
    130                 135                 140
```

<210> SEQ ID NO 37
<211> LENGTH: 141
<212> TYPE: PRT
<213> ORGANISM: Artificial
<220> FEATURE:
<223> OTHER INFORMATION: The variable region of the heavy chain (3A2)

<400> SEQUENCE: 37

Met Glu Phe Gly Leu Ser Trp Val Leu Leu Val Ala Leu Leu Arg Gly
1               5                   10                  15

Val Gln Cys Gln Val Gln Leu Val Glu Ser Gly Gly Asp Val Val Gln
            20                  25                  30

Pro Gly Arg Ser Leu Arg Leu Ser Cys Ala Ala Ser Gly Phe Thr Phe
        35                  40                  45

Asn Asn Tyr Gly Met His Trp Val Arg Gln Ala Pro Gly Lys Gly Leu
    50                  55                  60

Glu Trp Val Ala Val Val Trp Tyr Asp Gly Leu Ile Lys Tyr Tyr Ala
65                  70                  75                  80

Asp Ser Val Lys Gly Arg Phe Thr Ile Ser Arg Asp Asn Ser Lys Asn
                85                  90                  95

```
Thr Leu Tyr Leu Gln Met Asn Thr Leu Arg Ala Glu Asp Met Gly Val
        100                 105                 110

Tyr Tyr Cys Ala Arg Asp Leu Gln Pro Pro His Ser Pro Tyr Gly Met
        115                 120                 125

Asp Val Trp Gly Gln Gly Thr Thr Val Thr Val Ser Ser
        130                 135                 140

<210> SEQ ID NO 38
<211> LENGTH: 387
<212> TYPE: DNA
<213> ORGANISM: Artificial
<220> FEATURE:
<221> NAME/KEY: CDS
<222> LOCATION: (1)..(387)
<223> OTHER INFORMATION: The variable region of the kappa chain (3A2)

<400> SEQUENCE: 38 atg gcc tgg gtc tca ttc tac ctc acc ctc ctc act cac tgt gca ggg     48
Met Ala Trp Val Ser Phe Tyr Leu Thr Leu Leu Thr His Cys Ala Gly
1               5                   10                  15 tcc tgg gcc cag tct gtg ctg act cag cca ccc tca gcg tct ggg acc     96
Ser Trp Ala Gln Ser Val Leu Thr Gln Pro Pro Ser Ala Ser Gly Thr
            20                  25                  30 ccc ggg cag agg gtc acc atc tct tgt tct gga agc agc tcc aac atc    144
Pro Gly Gln Arg Val Thr Ile Ser Cys Ser Gly Ser Ser Ser Asn Ile
        35                  40                  45 gga agt aat gat gtc tat tgg tac cag aac ctc cca gga acg gcc ccc    192
Gly Ser Asn Asp Val Tyr Trp Tyr Gln Asn Leu Pro Gly Thr Ala Pro
    50                  55                  60 aaa ctc ctc atc tat aat aat aat caa cgg ccc tca ggg gtc cct gac    240
Lys Leu Leu Ile Tyr Asn Asn Asn Gln Arg Pro Ser Gly Val Pro Asp
65                  70                  75                  80 cga ttc tct ggc tcc aag tct ggc acc tca gcc tcc ctg gcc atc agt    288
Arg Phe Ser Gly Ser Lys Ser Gly Thr Ser Ala Ser Leu Ala Ile Ser
                85                  90                  95 ggg ctc cgg tcc gag gat gag gct gat tat tat tgt gca gca tgg gat    336
Gly Leu Arg Ser Glu Asp Glu Ala Asp Tyr Tyr Cys Ala Ala Trp Asp
            100                 105                 110 gac agc ctg act gtc tcc ttc gga act ggg acc aag gtc acc gtc cta    384
Asp Ser Leu Thr Val Ser Phe Gly Thr Gly Thr Lys Val Thr Val Leu
        115                 120                 125 ggt                                                                387
Gly

<210> SEQ ID NO 39
<211> LENGTH: 129
<212> TYPE: PRT
<213> ORGANISM: Artificial
<220> FEATURE:
<223> OTHER INFORMATION: The variable region of the kappa chain (3A2)

<400> SEQUENCE: 39

Met Ala Trp Val Ser Phe Tyr Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Asp Val Tyr Trp Tyr Gln Asn Leu Pro Gly Thr Ala Pro
    50                  55                  60
```

```
Lys Leu Leu Ile Tyr Asn Asn Asn Gln Arg Pro Ser Gly Val Pro Asp
 65                  70                  75                  80

Arg Phe Ser Gly Ser Lys Ser Gly Thr Ser Ala Ser Leu Ala Ile Ser
                 85                  90                  95

Gly Leu Arg Ser Glu Asp Glu Ala Asp Tyr Tyr Cys Ala Ala Trp Asp
            100                 105                 110

Asp Ser Leu Thr Val Ser Phe Gly Thr Gly Thr Lys Val Thr Val Leu
            115                 120                 125

Gly

<210> SEQ ID NO 40
<211> LENGTH: 456
<212> TYPE: DNA
<213> ORGANISM: Artificial
<220> FEATURE:
<221> NAME/KEY: CDS
<222> LOCATION: (1)..(456)
<223> OTHER INFORMATION: The variable region of the heavy chain (10C4)

<400> SEQUENCE: 40 atg gag ttt ggg ctg agc tgg ctt ttt ctt gtg gct att tta aaa ggt      48
Met Glu Phe Gly Leu Ser Trp Leu Phe Leu Val Ala Ile Leu Lys Gly
 1               5                  10                  15 gtc cag tgt gag gtg cag ctg ttg gag tct ggg gga ggc ttg gtc cag      96
Val Gln Cys Glu Val Gln Leu Leu Glu Ser Gly Gly Gly Leu Val Gln
            20                  25                  30 ccg ggg ggg tcc ctg aga ctc tcc tgt gca gcc tct gga ttc acc ttt     144
Pro Gly Gly Ser Leu Arg Leu Ser Cys Ala Ala Ser Gly Phe Thr Phe
        35                  40                  45 agc aac tat gcc atg agc tgg gtc cgc cag gct cca ggg aag ggg ctg     192
Ser Asn Tyr Ala Met Ser Trp Val Arg Gln Ala Pro Gly Lys Gly Leu
    50                  55                  60 gag tgg gtc tca gct att agt ggt ggt ggt gat tgg aca tac tac gca     240
Glu Trp Val Ser Ala Ile Ser Gly Gly Gly Asp Trp Thr Tyr Tyr Ala
 65                  70                  75                  80 gac tcc gtg aag ggc cga ttc tcc atc tcc agc gac aat tcc aag aac     288
Asp Ser Val Lys Gly Arg Phe Ser Ile Ser Ser Asp Asn Ser Lys Asn
                 85                  90                  95 acg ctg tat ctg caa atg aac agc ctg aga gcc gag gac acg gcc gta     336
Thr Leu Tyr Leu Gln Met Asn Ser Leu Arg Ala Glu Asp Thr Ala Val
            100                 105                 110 tat tac tgt gcg aaa gat gtc acg tat ttg tat gac agt agt ggt tat     384
Tyr Tyr Cys Ala Lys Asp Val Thr Tyr Leu Tyr Asp Ser Ser Gly Tyr
        115                 120                 125 tac tac ggg gga gcc gac cgc gat tat tac ttt gac tac tgg ggc cag     432
Tyr Tyr Gly Gly Ala Asp Arg Asp Tyr Tyr Phe Asp Tyr Trp Gly Gln
    130                 135                 140 gga acc ctg gtc acc gtc tcc tca                                     456
Gly Thr Leu Val Thr Val Ser Ser
145                 150

<210> SEQ ID NO 41
<211> LENGTH: 152
<212> TYPE: PRT
<213> ORGANISM: Artificial
<220> FEATURE:
<223> OTHER INFORMATION: The variable region of the heavy chain (10C4)

<400> SEQUENCE: 41

Met Glu Phe Gly Leu Ser Trp Leu Phe Leu Val Ala Ile Leu Lys Gly
 1               5                  10                  15
```

```
Val Gln Cys Glu Val Gln Leu Leu Glu Ser Gly Gly Gly Leu Val Gln
             20                  25                  30

Pro Gly Gly Ser Leu Arg Leu Ser Cys Ala Ala Ser Gly Phe Thr Phe
             35                  40                  45

Ser Asn Tyr Ala Met Ser Trp Val Arg Gln Ala Pro Gly Lys Gly Leu
             50                  55                  60

Glu Trp Val Ser Ala Ile Ser Gly Gly Gly Asp Trp Thr Tyr Tyr Ala
 65                  70                  75                  80

Asp Ser Val Lys Gly Arg Phe Ser Ile Ser Ser Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Lys Asp Val Thr Tyr Leu Tyr Asp Ser Ser Gly Tyr
             115                 120                 125

Tyr Tyr Gly Gly Ala Asp Arg Asp Tyr Tyr Phe Asp Tyr Trp Gly Gln
         130                 135                 140

Gly Thr Leu Val Thr Val Ser Ser
145                 150
```

<210> SEQ ID NO 42
<211> LENGTH: 390
<212> TYPE: DNA
<213> ORGANISM: Artificial
<220> FEATURE:
<221> NAME/KEY: CDS
<222> LOCATION: (1)..(390)
<223> OTHER INFORMATION: The variable region of the lamda chain (10C4)

<400> SEQUENCE: 42

```
atg ccc tgg gct ctt ctc ctc ctc acc ctc ctc act cac tgt gca ggg      48
Met Pro Trp Ala Leu Leu Leu Leu Thr Leu Leu Thr His Cys Ala Gly
 1               5                  10                  15 tcc tgg gcc cag tct gtg ctg act cag cca ccc tca gcg tct ggg acc      96
Ser Trp Ala Gln Ser Val Leu Thr Gln Pro Pro Ser Ala Ser Gly Thr
             20                  25                  30 ccc ggg cag agg gtc tcc atc tct tgt tct gga ggc agc tcc aac atc     144
Pro Gly Gln Arg Val Ser Ile Ser Cys Ser Gly Gly Ser Ser Asn Ile
         35                  40                  45 gga agt aat act gta aac tgg tac cag cag ctc cca gga acg gcc ccc     192
Gly Ser Asn Thr Val Asn Trp Tyr Gln Gln Leu Pro Gly Thr Ala Pro
     50                  55                  60 aga ctc ctc atc tat agc aat aat cag cgg ccc tta ggg gtc cct gac     240
Arg Leu Leu Ile Tyr Ser Asn Asn Gln Arg Pro Leu Gly Val Pro Asp
 65                  70                  75                  80 cga ttc tct gag tcc aag tct ggc acc tca gcc tcc ctg gcc atc agt     288
Arg Phe Ser Glu Ser Lys Ser Gly Thr Ser Ala Ser Leu Ala Ile Ser
                 85                  90                  95 ggg ctc cgg tct gag gat gag gct gat tat tac tgt gct gca tgg gat     336
Gly Leu Arg Ser Glu Asp Glu Ala Asp Tyr Tyr Cys Ala Ala Trp Asp
             100                 105                 110 gac agc ctg aat ggt tgg gtg ttc ggc gga ggg acc agg ctg acc gtc     384
Asp Ser Leu Asn Gly Trp Val Phe Gly Gly Gly Thr Arg Leu Thr Val
             115                 120                 125 cta ggt                                                             390
Leu Gly
    130
```

<210> SEQ ID NO 43
<211> LENGTH: 130
<212> TYPE: PRT

```
<213> ORGANISM: Artificial
<220> FEATURE:
<223> OTHER INFORMATION: The variable region of the lamda chain (10C4)

<400> SEQUENCE: 43

Met Pro Trp Ala Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
                20                  25                  30

Pro Gly Gln Arg Val Ser Ile Ser Cys Ser Gly Gly Ser Ser Asn Ile
            35                  40                  45

Gly Ser Asn Thr Val Asn Trp Tyr Gln Gln Leu Pro Gly Thr Ala Pro
    50                  55                  60

Arg Leu Leu Ile Tyr Ser Asn Asn Gln Arg Pro Leu Gly Val Pro Asp
65                  70                  75                  80

Arg Phe Ser Glu Ser Lys Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Asp Ser Leu Asn Gly Trp Val Phe Gly Gly Gly Thr Arg Leu Thr Val
            115                 120                 125

Leu Gly
    130

<210> SEQ ID NO 44
<211> LENGTH: 10
<212> TYPE: PRT
<213> ORGANISM: Artificial
<220> FEATURE:
<223> OTHER INFORMATION: epitope region of 5A7

<400> SEQUENCE: 44

Ile Gly Asn Cys Pro Ile Trp Val Lys Thr
1               5                   10
```